(12) United States Patent
Basiji et al.

(10) Patent No.: US 8,885,913 B2
(45) Date of Patent: Nov. 11, 2014

(54) DETECTION OF CIRCULATING TUMOR CELLS USING IMAGING FLOW CYTOMETRY

(71) Applicant: Amnis Corporation, Seattle, WA (US)

(72) Inventors: David A. Basiji, Seattle, WA (US); William E. Ortyn, Bainbridge Island, WA (US); Philip J. Morrissey, Bellevue, WA (US); Vidya Venkatachalam, Bellevue, WA (US)

(73) Assignee: Amnis Corporation, Seattle, WA (US)

( * ) Notice: Subject to any disclaimer, the term of this patent is extended or adjusted under 35 U.S.C. 154(b) by 12 days.

(21) Appl. No.: 14/040,398

(22) Filed: Sep. 27, 2013

(65) Prior Publication Data

US 2014/0030729 A1    Jan. 30, 2014

Related U.S. Application Data

(63) Continuation-in-part of application No. 13/396,333, filed on Feb. 14, 2012, now Pat. No. 8,548,219, which (Continued)

(51) Int. Cl.
*G06K 9/00* (2006.01)
*G01J 3/28* (2006.01)

(52) U.S. Cl.
USPC .......................................... 382/133; 356/326

(58) Field of Classification Search
USPC ................. 382/128, 133, 134; 600/410, 562; 356/451, 456, 326
See application file for complete search history.

(56) References Cited

U.S. PATENT DOCUMENTS 3,497,690 A    2/1970   Gunter et al.
3,555,280 A    1/1971   Richards, Jr.

(Continued)

FOREIGN PATENT DOCUMENTS

EP    0154404 A2    9/1985
EP    0280559 A2    8/1988
EP    0281327 A2    9/1988
EP    0372707 A2    6/1990
EP    0950890 A2    10/1999

(Continued)

OTHER PUBLICATIONS

Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," Reproduction, Fertility and Development 7: 799-809, 1995.

(Continued)

*Primary Examiner* — Rochelle-Ann J Blackman
(74) *Attorney, Agent, or Firm* — Lee & Hayes, PLLC

(57) ABSTRACT

An automated identification of the types of white blood cells in a blood sample facilitates the manual identification of cancerous or other abnormal blood cells in the sample. Classifiers are predetermined for each type of white blood cell and subsequently used to automatically process images of cells in a sample stained with a nuclear dye or stain. The classifiers each comprise a linear weighted combination of morphometric and photometric features previously selected for white blood cells that were identified using monoclonal antibody stains. Red blood cells and excess fluid are removed from a sample being processed upstream of an imaging region of the imaging system. A plurality of different types of images are produced for each cell by the imaging system enabling automated identification of the white blood cells. Images of any cells not thus identified are manually reviewed to detect cancerous or abnormal cells.

25 Claims, 16 Drawing Sheets

Related U.S. Application Data is a continuation of application No. 12/181,062, filed on Jul. 28, 2008, now Pat. No. 8,131,053, and a continuation-in-part of application No. 11/344,941, filed on Feb. 1, 2006, now Pat. No. 7,522,758, and a continuation of application No. 11/123,610, filed on May 4, 2005, now Pat. No. 7,450,229, and a continuation-in-part of application No. 10/628,662, filed on Jul. 28, 2003, now Pat. No. 6,975,400, which is a continuation-in-part of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/952,522, filed on Jul. 27, 2007, provisional application No. 60/649,373, filed on Feb. 1, 2005, provisional application No. 60/567,911, filed on May 4, 2004, provisional application No. 60/117,203, filed on Jan. 25, 1999, provisional application No. 60/240,125, filed on Oct. 12, 2000.

(56) References Cited

U.S. PATENT DOCUMENTS

| | | |
|---|---|---|
| 3,586,760 A | 6/1971 | Dillenburger |
| 3,922,069 A | 11/1975 | Kishikawa et al. |
| 4,313,734 A | 2/1982 | Leuvering |
| 4,414,575 A | 11/1983 | Yamamoto et al. |
| 4,635,293 A | 1/1987 | Watanabe |
| 4,662,742 A | 5/1987 | Chupp |
| 4,677,680 A | 6/1987 | Harima et al. |
| 4,703,017 A | 10/1987 | Campbell et al. |
| 4,737,932 A | 4/1988 | Baba |
| 4,770,992 A | 9/1988 | Van den Engh et al. |
| 4,777,525 A | 10/1988 | Preston, Jr. |
| 4,786,165 A | 11/1988 | Yamamoto et al. |
| 4,845,197 A | 7/1989 | Petersen et al. |
| 4,857,453 A | 8/1989 | Ullman et al. |
| 5,096,807 A | 3/1992 | Leaback |
| 5,107,522 A | 4/1992 | Kitayama et al. |
| 5,122,453 A | 6/1992 | Martin et al. |
| 5,141,609 A | 8/1992 | Sweedler et al. |
| 5,153,916 A | 10/1992 | Inagaki et al. |
| 5,159,397 A | 10/1992 | Kosaka et al. |
| 5,159,398 A | 10/1992 | Maekawa et al. |
| 5,159,642 A | 10/1992 | Kosaka |
| 5,247,339 A | 9/1993 | Ogino |
| 5,247,340 A | 9/1993 | Ogino |
| 5,257,182 A | 10/1993 | Luck et al. |
| 5,272,354 A | 12/1993 | Kosaka |
| 5,351,311 A | 9/1994 | Rogers et al. |
| 5,372,936 A | 12/1994 | Fraatz et al. |
| 5,422,712 A | 6/1995 | Ogino |
| 5,436,144 A | 7/1995 | Stewart et al. |
| 5,444,527 A | 8/1995 | Kosaka |
| 5,459,240 A | 10/1995 | Foxwell et al. |
| 5,471,294 A | 11/1995 | Ogino |
| 5,547,849 A | 8/1996 | Baer et al. |
| 5,548,349 A | 8/1996 | Mizuguchi et al. |
| 5,548,395 A | 8/1996 | Kosaka |
| 5,568,315 A | 10/1996 | Shuman |
| 5,596,401 A | 1/1997 | Kusuzawa |
| 5,621,460 A | 4/1997 | Hatlestad et al. |
| 5,625,048 A | 4/1997 | Tsien et al. |
| 5,633,503 A | 5/1997 | Kosaka |
| 5,664,388 A | 9/1997 | Chapman et al. |
| 5,674,743 A | 10/1997 | Ulmer |
| 5,686,960 A | 11/1997 | Sussman et al. |
| 5,695,934 A | 12/1997 | Brenner |
| 5,733,721 A | 3/1998 | Hemstreet, III et al. |
| 5,754,291 A | 5/1998 | Kain |
| 5,760,899 A | 6/1998 | Eismann |
| 5,764,792 A | 6/1998 | Kennealy |
| 5,784,162 A | 7/1998 | Cabib et al. |
| RE35,868 E | 8/1998 | Kosaka |
| 5,828,776 A | 10/1998 | Lee et al. |
| 5,831,723 A | 11/1998 | Kubota et al. |
| 5,844,670 A | 12/1998 | Morita et al. |
| 5,848,123 A | 12/1998 | Strommer |
| 5,855,753 A | 1/1999 | Trau et al. |
| 5,900,942 A | 5/1999 | Spiering |
| 5,926,283 A | 7/1999 | Hopkins |
| 5,929,986 A | 7/1999 | Slater et al. |
| 5,959,953 A | 9/1999 | Alon |
| 5,985,549 A | 11/1999 | Singer et al. |
| 5,986,061 A | 11/1999 | Pestka |
| 6,007,994 A | 12/1999 | Ward et al. |
| 6,007,996 A | 12/1999 | McNamara et al. |
| 6,014,468 A | 1/2000 | McCarthy et al. |
| 6,066,459 A | 5/2000 | Garini et al. |
| 6,108,082 A | 8/2000 | Pettipiece et al. |
| 6,115,119 A | 9/2000 | Sieracki et al. |
| 6,116,739 A | 9/2000 | Ishihara et al. |
| 6,156,465 A | 12/2000 | Cao et al. |
| 6,159,686 A | 12/2000 | Kardos et al. |
| 6,210,973 B1 | 4/2001 | Pettit |
| 6,211,955 B1 | 4/2001 | Basiji et al. |
| 6,229,913 B1 | 5/2001 | Nayar et al. |
| 6,249,314 B1 | 6/2001 | Yamamoto et al. |
| 6,249,341 B1 | 6/2001 | Basiji et al. |
| 6,256,096 B1 | 7/2001 | Johnson |
| 6,259,807 B1 | 7/2001 | Ravkin |
| 6,330,081 B1 | 12/2001 | Scholten |
| 6,330,361 B1 | 12/2001 | Mitchell et al. |
| 6,381,363 B1 | 4/2002 | Murching et al. |
| 6,473,176 B2 | 10/2002 | Basiji et al. |
| 6,507,391 B2 | 1/2003 | Riley et al. |
| 6,519,355 B2 | 2/2003 | Nelson |
| 6,522,781 B1 | 2/2003 | Norikane et al. |
| 6,532,061 B2 | 3/2003 | Ortyn et al. |
| 6,548,259 B2 | 4/2003 | Ward et al. |
| 6,549,664 B1 | 4/2003 | Daiber et al. |
| 6,563,583 B2 | 5/2003 | Ortyn et al. |
| 6,580,504 B1 | 6/2003 | Ortyn et al. |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,618,140 B2 | 9/2003 | Frost et al. |
| 6,620,591 B1 | 9/2003 | Dunlay et al. |
| 6,658,143 B2 | 12/2003 | Hansen et al. |
| 6,671,044 B2 | 12/2003 | Ortyn et al. |
| 6,671,624 B1 | 12/2003 | Dunlay et al. |
| 6,707,551 B2 | 3/2004 | Ortyn et al. |
| 6,716,588 B2 | 4/2004 | Sammak et al. |
| 6,727,066 B2 | 4/2004 | Kaser |
| 6,763,149 B2 | 7/2004 | Riley et al. |
| 6,778,263 B2 | 8/2004 | Ortyn et al. |
| 6,873,733 B2 | 3/2005 | Dowski, Jr. |
| 6,875,973 B2 | 4/2005 | Ortyn et al. |
| 6,906,792 B2 | 6/2005 | Ortyn et al. |
| 6,927,922 B2 | 8/2005 | George et al. |
| 6,934,408 B2 | 8/2005 | Frost et al. |
| 6,947,128 B2 | 9/2005 | Basiji et al. |
| 6,947,136 B2 | 9/2005 | Ortyn et al. |
| 6,975,400 B2 | 12/2005 | Ortyn et al. |
| 7,006,710 B2 | 2/2006 | Riley et al. |
| 7,033,819 B2 | 4/2006 | Kim et al. |
| 7,042,639 B1 | 5/2006 | McDowell |
| 7,050,620 B2 | 5/2006 | Heckman |
| 7,057,732 B2 | 6/2006 | Jorgenson et al. |
| 7,079,708 B2 | 7/2006 | Riley et al. |
| 7,087,877 B2 | 8/2006 | Ortyn et al. |
| 7,139,415 B2 | 11/2006 | Finkbeiner |
| 7,180,673 B2 | 2/2007 | Dowski, Jr. |
| 7,190,832 B2 | 3/2007 | Frost et al. |

(56) References Cited

U.S. PATENT DOCUMENTS

| | | | |
|---|---|---|---|
| 7,221,457 B2 | 5/2007 | Jorgenson et al. | |
| 7,289,205 B2 | 10/2007 | Yaroslavsky et al. | |
| 7,315,357 B2 | 1/2008 | Ortyn et al. | |
| 7,450,229 B2 | 11/2008 | Ortyn et al. | |
| 7,522,758 B2 | 4/2009 | Ortyn et al. | |
| 7,567,695 B2 | 7/2009 | Frost et al. | |
| 7,667,761 B2 | 2/2010 | Thomas | |
| 7,925,069 B2 | 4/2011 | Ortyn et al. | |
| 8,131,053 B2 | 3/2012 | Ortyn et al. | |
| 8,548,219 B2 * | 10/2013 | Ortyn et al. | 382/133 |
| 2001/0006416 A1 | 7/2001 | Johnson | |
| 2001/0011018 A1 | 8/2001 | Baum et al. | |
| 2001/0012620 A1 | 8/2001 | Rich | |
| 2002/0030812 A1 | 3/2002 | Ortyn et al. | |
| 2002/0126275 A1 | 9/2002 | Johnson | |
| 2002/0146734 A1 | 10/2002 | Ortyn et al. | |
| 2003/0048931 A1 | 3/2003 | Johnson et al. | |
| 2003/0049701 A1 | 3/2003 | Muraca | |
| 2003/0059093 A1 | 3/2003 | Rosania et al. | |
| 2003/0104439 A1 | 6/2003 | Finch | |
| 2004/0093166 A1 | 5/2004 | Kil | |
| 2004/0111220 A1 | 6/2004 | Ochs et al. | |
| 2004/0241759 A1 | 12/2004 | Tozer et al. | |
| 2005/0014129 A1 | 1/2005 | Cliffel et al. | |
| 2006/0246481 A1 | 11/2006 | Finch et al. | |
| 2006/0257884 A1 | 11/2006 | Brawley et al. | |
| 2007/0054350 A1 | 3/2007 | Walker | |
| 2008/0240539 A1 | 10/2008 | George et al. | |
| 2008/0317325 A1 | 12/2008 | Ortyn et al. | |
| 2009/0202130 A1 | 8/2009 | George et al. | |
| 2010/0232675 A1 | 9/2010 | Ortyn et al. | |

FOREIGN PATENT DOCUMENTS

| | | |
|---|---|---|
| EP | 1316793 A1 | 6/2003 |
| JP | 62134559 A | 6/1987 |
| JP | 2004522163 A | 7/2004 |
| WO | WO8808534 A1 | 11/1988 |
| WO | WO9010715 A1 | 9/1990 |
| WO | WO9520148 A1 | 7/1995 |
| WO | WO9726333 A1 | 7/1997 |
| WO | WO9853093 A1 | 11/1998 |
| WO | WO9853300 A2 | 11/1998 |
| WO | WO9924458 A1 | 5/1999 |
| WO | WO9964592 A2 | 12/1999 |
| WO | WO0006989 A2 | 2/2000 |
| WO | WO0014545 A1 | 3/2000 |
| WO | WO0042412 A1 | 7/2000 |
| WO | WO0111341 A2 | 2/2001 |
| WO | WO0146675 A2 | 6/2001 |
| WO | WO0217622 A1 | 2/2002 |
| WO | WO0218537 A2 | 3/2002 |
| WO | WO0231182 A2 | 4/2002 |
| WO | WO0235474 A1 | 5/2002 |
| WO | WO02073200 A1 | 9/2002 |
| WO | WO02079391 A2 | 10/2002 |
| WO | WO2005090945 A1 | 9/2005 |
| WO | WO2005098430 A2 | 10/2005 |

OTHER PUBLICATIONS

Robbins et al., "Use of Fluorescence in Situ Hybridization (FISH) to Assess Effects of Smoking, Caffeine, and Alcohol on Aneuploidy Load in Sperm of Healthy Men," Environmental and Molecular Mutagenesis 30: 175-183, 1997.

Rufer et al., "Telomere length dynamics in human lymphocyte subpopulations measured by flow cytometry," Nature Biotechnology 16:743-747, Aug. 1998.

Salzman et al., "Light Scatter: Detection and Usage," Current Protocols in Cytometry Supplement 9: 1.13.1-1.138.8, 1999.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." Cytometry: 48:194-201.

Schmid et al., "Evaluation of inter-scorer and inter-laboratory reliability of the mouse epididymal sperm aneuploidy (m-ESA) assay," Mutagenesis vol. 16, No. 3: 189-195, 2001.

Schmid et al., "Simultaneous Flow Cytometric Analysis of Two Cell Surface Markers, Telomere Length, and DNA Content," Cytometry 49: 96-105, 2002.

Schwerin et al., "Quantification of Y Chromosome Bearing Spermatozoa of Cattle Using in Situ Hybridization," Molecular Reproduction and Development 30: 39-43, 1991.

Shi et al., "Aneuploidy in human sperm: a review of the frequency and distribution of aneuploidy, effects of donor age and lifestyle factors," Cytogenetics and Cell Genetics 90: 219-226, 2000.

Timm et al., "Amplification and Detection of a Y-Chromosome DNA Sequence by Fluorescence in Situ Polymerase Chain Reaction and Flow Cytometry Using Cells in Suspension," Cytometry (Communications in Clinical Cytometry) 22: 250-255, 1995.

Timm et al., "Fluorescent in Situ Hybridization En Suspension (FISHES) Using Digoxigenin-qLabeled Probes and Flow Cytometry," Biotechniques vol. 12, No. 3: 362-367, 1992.

Trask et al., "Fluorescence in situ hybridization to interphase cell nuclei in suspension allows flow cytometric analysis of chromosome content and microscopic analysis of nuclear organization," Human Genetics 78:251-259, 1988.

Tucker et al., "Extended depth of field and aberration control for inexpensive digital microscope systems" Optics Express vol. 4, No. 11:467-474, May 24, 1999.

van Dekken et al., "Flow Cytometric Quantification of Human Chromosome Specific Repetitive DNA Sequences by Single and Bicolor Fluorescent in Situ Hybridization to Lymphocyte Interphase Nuclei," Cytometry 11: 153-164, 1990.

van den Berg et al., "Detection of Y Chromosome by in situ Hybridization in Combination with Membrane Antigens by Two-Color Immunofluorescence," Laboratory Investigation vol. 64, No. 5: 623-628, 1991.

Wang, Fu-sheng and Fumio Kubota. 2002. "A Novel Apoptosis Research Method With Imaging-Combined Flow Cytometer and HITC OR IR-125 Staining." Cytometry: 50:267-274.

Weber-Matthieson et al., "Rapid immunophenotypic characterization of chromosomally aberrant cells by the new FICTION method," Cytogenetics Cell Genetics 63: 123-125, 1993.

Weber-Matthieson et al., "Simultaneous Fluorescence Immunophenotyping and Interphase Cytogenetics: A Contribution to the Characterization of Tumor Cells," Journal of Histochemistry and Cytochemistry vol. 40, No. 2:171-175, 1992.

Wietzorrek, Joachim et al. 1999. "A New Multiparameter Flow Cytometer: Optical and Electrical Cell Analysis in Combination With Video Microscopy in Flow." Cytometry: 35:291-301.

Wyrobek et al., "Detection of Sex Chromosomal Aneuploidies X-X, Y-Y, and X-Y, in Human Sperm Using Two-Chromosome Fluorescence in Situ Hybridization," American Journal of Medical Genetics 53: 1-7, 1994.

Wyrobek et al., "Fluorescence in Situ Hybridization to Y Chromosomes in Decondensed Human Sperm Nuclei," Molecular Reproduction and Development 27: 200-208, 1990.

Wyrobek et al., "Smokers produce more aneuploid sperm than non-smokers," The American Society of Human Genetics, 45th Annual Meeting, A131: 737, Oct. 24-28, 1995.

Amman et al., "Fluorescent-Oligonucleotide Probing of Whole Cells for Determinative, Phylogenetic, and Environmental Studies in Microbiology," Journal of Bacteriology vol. 172, No. 2: 762-770, Feb. 1990.

Arkesteijn et al. "Chromosome Specific DNA Hybridization in Suspension for Flow Cytometric Detection of Chimerism in Bone Marro Transplantation and Leukemia," Cytometry 19: 353-360, Apr. 1995.

Baines et al., "Flow Cytometric Quantitation of Sequence-Specific mRNA in Hemopoietic Cell Suspension by Primer-Induced in Situ (PRINS) Fluorescent Nucleotide Labeling," Experimental Cell Research 208: 321-326, Sep. 1993.

Barren III et al., "Method for Identifying Prostate Cells in Semen Using Flow Cytometry," The Prostate 36: 181-188, Aug. 1998.

Bauman et al., "Flow Cytometric Detection of Ribosomal RNA in Suspended Cells by Fluorescent in Situ Hybridization," Cytometry 9: 517-524, Nov. 1998.

(56) References Cited

OTHER PUBLICATIONS

Baumgartner et al., "Automated Evaluation of Frequencies of Aneuploid Sperm by Laser-Scanning Cytometry (LSC)," Cytometry 44: 156-160, Jun. 2001.
Ben-Eliezer et al., "All-optical extended depth of field imaging system," Journal of Optics A: Pure and Applied Optics 5: SI64-S169, Sep. 2003.
Biggs et al., "Acceleration of iterative image restoration algorithms" Applied Optics vol. 36, No. 8: 1766-1775, Mar. 10, 1997.
Boyle et al., "Isolation and Initial Characterization of a Large Repeat Sequence Element Specific to Mouse Chromosome 8," Genomics vol. 12, No. 3: 517-525, Mar. 1992.
Callet-Bauchu et al., "Distribution of the cytogenetic abnormality +i(3)(q10) in persistent polyclonal B-cell lymphocytosis: a Fiction study in three cases," British Journal of Haematology 99: 531-536, Dec. 1997.
Ding et al., "Characterization and Quantitation of NF-KB Nuclear Translocation Induced by Interleukin-1 and Tumor Necrosis Factor-u," The Journal of Biological Chemistry vol. 273, No. 44: 28897-28905, Oct. 30, 1998.
Disteche et al., "Isolation and characterization of two repetitive DNA fragments located near the centromere of the mouse X chromosome," Cytogenetics and Cell Genetics 39: 262-268, 1985.
Dragowska et al., "Measurement of DNA repeat sequence by flow cytometry," Cytometry Supplement 7: 51, Oct. 1994.
Engvall, Eva. "Enzyme Immunoassay ELISA and EMIT," Methods in Enzymology vol. 70, Part A: 419-439, Dec. 1980.
Femandez-Lago et al., "Fluorescent Whole-Cell Hybridization with 16S rRNA-Targeted Oligonucleotide Probes to Identify *Brucella* spp. By Flow Cytometry," Journal of Clinical Microbiology vol. 38, No. 7: 2768-2771, Jul. 2000.
Ferraro et al., "Extended focused image in microscopy by digital holography," Optics Express, vol. 13, No. 18: 6738-6749, Sep. 2005.
George, Thaddeus, David A. Basiji, Brian E. Hall, David H. Lynch, William E. Ortyn, David J. Perry, Michael J. Seo, Cathleen A. Zimmerman, and Philip J. Morrissey. "Distinguishing Modes of Cell Death Using the ImageStream Multispectral Imaging Flow Cytometer" Cytometry Part A 59A:237-245, Jun. 2004.
George et al., "Extended depth of field using a logarithmic asphere" Journal of Optics A: Pure and Applied Optics 5: SI57-S163, Sep. 2003.
George, Thaddeus C., Stacey L. Fanning, Patricia Fitzgeral-Bocarsly, Ricardo B. Medeiros, Sarah Highfill, Yoji Shimizu, Brian E. Hall, Keith Frost, David Basiji, William E. Ortyn, Philip J. Morrissey, David H. Lynch. "Quantitative measurement of nuclear translocation events using similarity analysis of multispectral cellular images obtained in flow," Journal of Immunological Methods, 311, Apr. 2006, 117-129.
Gordy, Claire et al., "Visualization of antigen presentation by actin-mediated targeting of glycolipid-enriched membrane domains to the immune synapse of B cell APCs." Journal of Immunology, vol. 172, No. 4, Feb. 15, 2004. pp. 2030-2038, XP002481372 ISSN: 0022-1767.
Hecht, Eugene. "Optics 4th ed." 2002. Addison-Wesley Longman, Inc., XP-002465391. ISBN: 0-8053-8566-5.
Hultdin et al., "Telomere analysis by fluorescence in situ hybridization and flow cytometry," Nucleic Acids Research vol. 26, No. 16: 3651-3656, Aug. 15, 1998.
Translated Japanese Office Action mailed Sep. 9, 2011 for Japanese patent application No. 2007-554187, a counterpart foreign application of US patent No. 7,522,758, 2 pages.
Kubota, F., "Analysis of red cell and platelet morphology using an imaging-combined flow cytometer." Clin. Lab. Haem., Apr. 2003, 25:71-76.
Kubota, Fumio et al., "Flow Cytometer and Imaging Device Used in Combination." Cytometry, Oct. 1995, 21:129-132.
Lauzon et al., "Flow Cytometric Measurement of Telomere Length," Cytometry 42: 159-164, Jun. 2000.
Levron et al., "Sperm chromosome abnormalities in men with severe male factor infertility who are undergoing in vitro fertilization with intracytoplasmic sperm injection," Fertility and Sterility vol. 76, No. 3: 479-484, Sep. 2001.
Lowe et al., "Aneuploid epididymal sperm detected in chromosomally normal and Robertsonian translocation-bearing mice using a new three-chromosome FISH method," Chromosoma 105: 204-210, 1996.
Majno et al., "Apoptosis, Oncosis, and Necrosis, An Overview of Cell Death," American Journal of Pathology vol. 146, No. 1: 3-15, Jan. 1, 1995.
Martin et al., "Detection of aneuploidy in human interphase spermatozoa by fluorescence in situ hybridization (FISH)," Cytogenetics and Cell Genetics 64: 23-26, 1993.
Nautiyal et al., "17B-Estradiol induces nuclear translocation of CrkL at the window of embryo implantation," Biochemical and Biophysical Research Communications 318: 103-112, 2004.
Non-Final Office Action for U.S. Appl. No. 12/181,062, mailed on Jun. 14, 2011, William E. Ortyn et al., "Detection of Circulating Tumor Cells Using Imaging Flow Cytometry ", 28 pages.
Non-Final Office Action for U.S. Appl. No. 12/631,795, mailed on Aug. 14, 2012, William Ortyn et al., "Blood and Cell Analysis Using an Imaging Flow Cytometer", 9 pages.
Non-Final Office Action for U.S. Appl. No. 13/396,33, mailed on Sep. 12, 2012, William Ortyn et al., "Detection of Circulating Tumor Cells Using Imaging Flow Cytometry", 6 pages.
Office action for U.S. Appl. No. 13/798,442, mailed on Sep. 23, 2013, Ortyn et al., "Blood and Cell Analysis Using an Imaging Flow Cytometer", 5 pages.
Oberholzer et al., "Methods in quantitative image analysis," Histochem Cell Biol, vol. 105: 333-355, May 1996.
Ong, S.H. and P.M. Nickolls, "Analysis of MTF Degradation in the Imaging of Cells in a Flow System." International Journal of Imaging Systems & Technology, Autum(Fall) 1994, 5:243-250.
Ong, Sim Hen, "Development of a System for Imaging and Classifying Biological Cells in a Flow Cytometer," Doctor of Philosophy Thesis. University of Sydney, School of Electrical Engineering, Aug. 1985.
Ong, S.H. et al., "Development of an Image Flow Cytometer." Analytical and Quantitative Cytology and Histology. XIVth International Conference on Medical and Biological Engineering and the VIIth International Conference on Medical Physics, Finland, Aug. 1987, 375-382.
Ong, S.H. and P.M. Nickolls, "Optical Design in a Flow System for Imaging Cells." Sciences in Medicine, Jun. 1991, 14:2:74-80.
Ortyn et al., "Extended Depth of Field Imaging for High Speed Cell Analysis" Cytometry Part A 71A: 215-231, Apr. 2007.
Pala et al., "Flow cytometric measurement of intracellular cytokines,"Journal of Immunological Methods 243: 107-124, Mar. 2000.
Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," Human Reproduction vol. 14, No. 5: 1266-1273, May 1999.
Patterson et al., "Detection of HIV-1 DNA and Messenger RNA in Individual Cells by PCR-Driven in Situ Hybridization and Flow Cytometry," Science 260: 976-979, May 14, 1993.
Perreault et al., "The Role of Disulfide Bond Reduction during Mammalian Sperm Nuclear Decondensation in Vivo," Developmental Biology 101: 160-167, Jan. 1984.
Pinkel et al., "Cytogenetic analysis using quantitative, high sensitivity, fluorescence hybridization," Proceedings of the National Academy of Sciences: Genetics 83: 2934-2938, May 1986.
Pollice et al., "Sequential Paraformaldehyde and Methanol Fixation for Simultaneous Flow Cytometric Analysis of DNA, Cell Surface Proteins, and Intracellular Proteins," Cytometry 13: 432-444, 1992.
Ried et al., "Simultaneous visualization of seven different DNA probes by in situ hybridization using combinatorial fluorescence and digital imaging microscopy," Proceedings of the National Academy of Sciences: Genetics 89:1388-1392, Feb. 1992.

(56) References Cited

OTHER PUBLICATIONS

Robbins et al., "Aneuploidy in sperm of Hodgkin's disease patients receiving NOVP chemotherapy," The American Journal of Human Genetics vol. 55, No. 3- Supplement: A68 (371), Sep. 1994.

Robbins et al., "Detection of Aneuploid Human Sperm by Fluorescence in Situ Hybridization: Evidence for a Donor Difference in Frequency of Sperm Disomic for Chromosomes 1 and Y," The American Journal of Human Genetics, 52: 799-807, Apr. 1993.

* cited by examiner

Example - Granulocyte Classifier (370 features)

| # | Feature | Value |
|---|---|---|
| 1 | Mean Pixel_Morphology(M09,Ch09)_Ch09 | -0.55 |
| 2 | Intensity_MC_Ch01 | -0.55 |
| 3 | Modulation_M06_Ch06 | 0.55 |
| 4 | Bright Detail Intensity R7_MC_Ch07 | 0.55 |
| 5 | Contrast_M06_Ch06 | 0.55 |
| 6 | Mean Pixel_M09_Ch09 | -0.55 |
| 7 | Mean Pixel_Morphology(M01,Ch01)_Ch01 | -0.53 |
| 8 | Mean Pixel_M01_Ch01 | -0.53 |
| 9 | Mean Pixel_Object(M09,Ch09,Tight)_Ch09 | -0.52 |
| 10 | Intensity_MC_Ch09 | -0.5 |
| 11 | Contrast_Object(M06,Ch06,Tight)_Ch06 | 0.48 |
| 12 | Median Pixel_M09_Ch09 | -0.46 |
| 13 | Mean Pixel_Object(M01,Ch01,Tight)_Ch01 | -0.45 |
| 14 | Bright Detail Intensity R3_MC_Ch06 | 0.44 |
| 15 | Modulation_Object(M06,Ch06,Tight)_Ch06 | 0.44 |
| 16 | Intensity_Skeleton(Morphology(M06,Ch06),Ch06,Thin)_Ch06 | 0.44 |
| 17 | Median Pixel_M06_Ch06 | 0.44 |
| 18 | Mean Pixel_M06_Ch06 | 0.43 |
| 19 | Mean Pixel_Valley(M09,Ch09,3)_Ch09 | -0.43 |
| 20 | Mean Pixel_Valley(Morphology(M09,Ch09),Ch09,3)_Ch09 | -0.43 |
| 21 | Raw Min Pixel_MC_Ch09 | -0.42 |
| 22 | Mean Pixel_Object(M06,Ch06,Tight)_Ch06 | 0.42 |
| ... | | |
| 368 | Circularity_M06 | 0.17 |
| 369 | Length_Morphology(M07,Ch07) | 0.17 |
| 370 | Minor Axis_Morphology(M06,Ch06) | 0.17 |

SEPARATES EOSINOPHILS, NEUTROPHILS, AND BASOPHILS FROM LYMPHOCYTES AND MONOCYTES

GRANULOCYTES SCORE POSITIVE NON-GRANULOCYTES SCORE NEGATIVE

FIG. 7

SENSITIVITY AND SPECIFICITY ANALYSIS $$SENSITIVITY = \frac{\text{\# OF TRUE POSITIVES}}{\text{\# OF TRUE POSITIVES } + \text{ \# OF FALSE NEGATIVES}}$$

$$SPECIFICITY = \frac{\text{\# OF TRUE NEGATIVES}}{\text{\# OF TRUE NEGATIVES } + \text{ \# OF FALSE POSITIVES}}$$

DEFINITIONS

- *TRUE POSITIVE* – THE GROUP OF CELLS CLASSIFIED AS WITHIN A GIVEN SUBSET THAT ARE ALSO WITHIN THE GOLD STANDARD TRUTH FOR THAT SUBSET

- *FALSE NEGATIVE* – THE GROUP OF CELLS CLASSIFIED AS NOT WITHIN A GIVEN SUBSET THAT ARE ALSO WITHIN THE GOLD STANDARD TRUTH FOR THAT SUBSET

- *TRUE NEGATIVE* – THE GROUP OF CELLS CLASSIFIED AS NOT WITHIN A GIVEN SUBSET THAT ARE ALSO NOT WITHIN GOLD STANDARD TRUTH FOR THAT SUBSET

- *FALSE POSITIVE* – THE GROUP OF CELLS CLASSIFIED AS WITHIN A GIVEN SUBSET THAT ARE NOT WITHIN THE GOLD STANDARD TRUTH FOR THAT SUBSET

- *GOLD STANDARD* – THE GROUP OF CELLS CLASSIFIED FOR EACH SUBSET VIA IMMUNOFLUORESCENT STAINING

RELATIVE CONCENTRATIONS (LOG SCALE) OF 5 COMPONENTS FOR 8 SAMPLES (SAMPLES #1 AND #4 CORRESPOND TO THE SAME DONOR) USING IMMUNOFLUORESCENCE (*IMM), CLASSIFIER (*CLASS), AND CLASSIFIER ON DAPI ONLY (*DAPI).

DETECTION OF CIRCULATING TUMOR CELLS USING IMAGING FLOW CYTOMETRY

RELATED APPLICATIONS

This application is a continuation-in-part of a copending patent application Ser. No. 13/396,333, filed on Feb. 14, 2012, which is a continuation of a copending patent application Ser. No. 12/181,062, filed on Jul. 28, 2008 (now issued as U.S. Pat. No. 8,131,053), which itself is based on a prior copending provisional application Ser. No. 60/952,522, filed on Jul. 27, 2007, the benefit of the filing dates of which is hereby claimed under 35 U.S.C. §120 and 35 U.S.C. §119(e). U.S. Pat. No. 8,131,053 is a continuation-in-part of a copending patent application Ser. No. 11/344,941, filed on Feb. 1, 2006 (now issued as U.S. Pat. No. 7,522,758), which itself is based on a prior provisional application Ser. No. 60/649,373, filed on Feb. 1, 2005, the benefit of the filing dates of which is also hereby claimed under 35 U.S.C. §120 and 35 U.S.C. §119(e).

Prior copending U.S. Pat. No. 7,522,768 is also a continuation application based on a prior copending conventional application Ser. No. 11/123,610, filed on May 4, 2005 (now issued as U.S. Pat. No. 7,450,229), which itself is based on a prior provisional application Ser. No. 60/567,911, filed on May 4, 2004, and which is also a continuation-in-part of prior patent application Ser. No. 10/628,662, filed on Jul. 28, 2003 (now issued as U.S. Pat. No. 6,975,400), which itself is a continuation-in-part application of prior patent application Ser. No. 09/976,257, filed on Oct. 12, 2001 (now issued as U.S. Pat. No. 6,608,682), which itself is a continuation-in-part application of prior patent application Ser. No. 09/820,434, filed on Mar. 29, 2001 (now issued as U.S. Pat. No. 6,473,176), which itself is a continuation-in-part application of prior patent application Ser. No. 09/538,604, filed on Mar. 29, 2000 (now issued as U.S. Pat. No. 6,211,955), which itself is a continuation-in-part application of prior application patent application Ser. No. 09/490,478, filed on Jan. 24, 2000 (now issued as U.S. Pat. No. 6,249,341), which itself is based on prior provisional patent application Ser. No. 60/117,203, filed on Jan. 25, 1999, the benefit of the filing dates of which is hereby claimed under 35 U.S.C. §120 and 35 U.S.C. §119 (e). Prior copending U.S. Pat. No. 6,608,682, noted above, is also based on prior provisional application Ser. No. 60/240,125, filed on Oct. 12, 2000, the benefit of the filing date of which is hereby claimed under 35 U.S.C. §119(e).

BACKGROUND

Carcinomas are the most common form of cancer, and are responsible for the majority of cancer-related deaths worldwide. Early detection of cancer significantly improves a prognosis, as evidenced by the 70% reduction in mortality in cervical cancer that was observed after the Papanicolaou test became accepted as a routine annual examination in the United States. Likewise, mortality rates from breast cancer have been reduced by up to 30% because of earlier detection through manual examination and mammograms. Unfortunately, the relative inaccessibility of most body tissues currently limits the breadth of cancer screening. Even when tumors are detected by existing techniques and removed surgically, there is a strong inverse correlation between tumor size and out-come, such that cancer survival rates are higher when tumors are detected early and removed while the tumors are relatively small in size.

The analysis of accessible body fluids for the detection of neoplastic cells should greatly facilitate earlier cancer detection, and the detection of micro-metastases and/or cells originating from a solid tumor in body fluids of patients who have early stage cancer could have a substantial impact on optimizing therapeutic regimens and, thus, long-term prognosis. Unfortunately, even when cancer is present in a patient, the relative number of cancer cells in readily accessible bodily fluids, such as blood, can be on the order of one cell per milliliter of fluid, making cancer detection by sampling bodily fluids very challenging. Classic manual microscopy-based analysis, although the gold standard in diagnostics, lacks the throughput required to identify rare cell populations consistently and with confidence, because the time required for manual review of millions of cells in a blood sample is simply too great to be practical. Flow cytometry offers much higher data acquisition and sample processing rates, but flow cytometry depends largely on the availability of fluorescently labeled markers to discriminate between normal cells and neoplastic cells. This requirement presents a challenge, since the tumor-specific markers may not be known ahead of time and even when they are, the markers expressed by circulating tumor cells can differ from those expressed within the tumor of origin.

The use of an antibody-based approach to address this problem depends on ectopic expression of a normal antigenic epitope, formation of a new epitope through genetic mutation or recombination, or consistent modulation of the expression of a marker expressed in transformed and non-transformed cells. Further, the cost of antibodies for use in detecting cancerous cells may be prohibitive in a screening context. The approach is confounded further by the diversity of neoplastic transformations and genetic heterogeneity in the human population.

In contrast to single- or multi-parameter antibody-based techniques, cellular morphology analysis is a further effective means of cancer screening. For instance, dysplastic and neoplastic cells can be detected in lung sputum on the basis of morphology. Likewise, exfoliated cells collected from bladder washings of bladder cancer patients have been shown to have distinct morphologic and genetic changes. Dysplastic morphology is also the primary diagnostic criterion in Papanicolaou smears, where microscope-based automated morphologic analysis is shown to be effective and approved by the Food and Drug Administration for primary screening.

Studies have indicated that cancer cells exhibit morphological characteristics that can be used to differentiate cancer cells from normal cells, however, most instruments capable of acquiring cellular images having enough detail to enable such morphological characteristics to be discerned do not have the throughput required to be able to detect very small numbers of cancer cells hidden in relatively large populations of normal cells. This problem is significant, because studies have indicated that the blood of a majority of patients who have had metastatic carcinomas contains fewer than one detectable carcinoma cell per 7.5 mL of blood, which is below the current threshold of five circulating tumor cells necessary to make a statistically robust diagnosis.

The above-noted commonly assigned related applications and issued patents disclose systems and apparatus for rapidly acquiring detailed cellular images from relatively large populations of cells. Using these detailed images, relatively small numbers of cancer cells present in a larger population can be statistically detected.

A common approach for detecting cancer cells seeks to reduce the effort required in manual microscopy-based analysis of a blood sample by eliminating or reducing the red blood cells and white blood cells in a sample being manually microscopically analyzed. The use of surface markers specific to cancer cells or specific to normal cells, as well as morphology and other features useful as a basis for reducing the population of white blood cells in a sample can be employed for this purpose. However, the procedure used to reduce the numbers of white blood cells in the sample that is to be manually analyzed may also substantially reduce the cancer cells in the sample, or may leave too many white blood cells in the sample. Typically, a person can realistically only manually review a few hundred cells in a session, since the manual analysis is visually tiring.

An alternative approach may be desirable that does not attempt to automatically analyze the images to directly identify cancerous cells. It would be desirable to reduce the effort required for manual review of images to detect cancerous or other types of abnormal cells. Thus, it would be desirable to derive a relatively small subset of images from all of the images that are automatically created, where the small subset of images are of objects that have not been automatically classified as normal components of blood, such as white blood cells. It would then be practical and efficient to manually review these images in the small subset to confirm whether the objects in the images are indeed cancer cells. Such an approach should increase the likelihood of identifying cancerous cells, by limiting the manual review to images of cells that may likely be abnormal.

In connection with such an approach, it would be desirable to develop a method for identifying specific features in images of white blood cells for use by an instrument to automatically classify each of the five types of white blood cells, so that the instrument can readily identify each type with an acceptable sensitivity (i.e., an acceptable percentage of false negative errors), and with an acceptable specificity (i.e., an acceptable percentage of false positive errors, which would result in wrongly classifying the type of a white blood cell). Sensitivity and specificity are discussed in greater detail below, in connection with FIG. 13. It would be desirable to then use these feature sets to define classifiers to enable an imaging system to automatically determine if a cell that is imaged is one of the five types of white cells, or instead, is an unidentified type of cell that may be a cancerous or other type of abnormal cell.

SUMMARY

This application specifically incorporates by reference the disclosures and drawings of each patent application and issued patent identified above as a related application.

A method is disclosed herein for detecting cancerous or other types of abnormal cells in a blood sample. The method provides for removing most of the red blood cells from the blood sample, leaving a residual sample that primarily includes white blood cells and a fluid. Nuclei of cells in the sample are stained using a nuclear dye or stain, producing stained cells. The stained cells are imaged to simultaneously produce a plurality of different types of images of each stained cell. The plurality of different types of images are then automatically analyzed to detect features of the images, and based on classifiers previously defined as a function of specific features selected for distinguishing each of a plurality of different types of white blood cells, any of the stained cells that are automatically identified by the instrument as being one of the five types of white blood cells is included in a first subset of the imaged cells. The cells that were not identified as being any type of white blood cell are included in a second subset of the imaged cells. Images of the second subset can then be manually reviewed to determine whether any of the cells in the second subset are cancerous cells or other types of abnormal cells. Since there are relatively much fewer images in the second subset, the work effort required to manually review those images is much less than would be required in the conventional approach to review images that include those of white blood cells.

Staining the nuclei of cells in the residual sample includes fixation and permeabilization of the cells before staining the nuclei with the nuclear dye or stain.

Removal of the red blood cells before cells in the sample are imaged can be accomplished by applying either a filtering process, a depletion process based on red cell surface chemistry, differential lysis of the red blood cells, or by using an acoustic technique to separate the red blood cells and excess fluid from the blood sample, so that the remainder comprises the residual sample.

The nuclear dye or stain can include either 4',6-diamidino-2-phenylindole (DAPI); a cell-permeant cyanine nucleic acid dye (e.g., SYTO™); an A-T intercalating anthraquinone stain (e.g., DRAQ5™); 7-Aminoactinomycin D (7-AAD); or propidium iodide, although other nuclear dyes or stains may also be used.

In an exemplary embodiment discussed below, imaging the stained cells to simultaneously produce a plurality of different types of images comprises processing the stained cells with a flow cytometer that simultaneously forms a plurality of images of cells passing through an imaging region of the flow cytometer, using light in a plurality of different channels. The light in each channel is used to produce a different one of the plurality of different types of images on separate portions of a light detector. The plurality of different types of images that are produced include a bright field image, a side scatter image, and a nuclear fluorescence image.

Automatically evaluating the plurality of different types of images to detect features of the images involves automatically detecting morphometric parameters, and photometric parameters evident in the plurality of different types of images. Identifying a first subset of the stained cells as specific types of white blood cells in the blood sample comprises applying the classifiers that were previously determined to the morphometric and photometric parameters detected in the images of the cells; each classifier is applied to detect a different type of white blood cell.

The method can further include using linear discriminant analysis to determine the classifier for each different type of white blood cell by forming a weighted linear combination of features for each classifier. The features for determining each classifier for each different type of white blood cell can be selected by evaluating populations of donor blood cells that were stained with the nuclear dye or stain, and with monoclonal antibodies appropriate for each type of white blood cell, using features related to the use and effects of the monoclonal antibodies to identify each different type of white blood cells in the populations of donor cells. The features related to the nuclear dye or stain for each type of white blood cell thus identified that are found to provide the greatest discrimination to distinguish a type of white blood cell from other types of white blood cells are then selected for use in the linear weighted combination of features for that type of white blood cell.

Another aspect of the present technology is directed to apparatus for use in facilitating the imaging of cancerous or other types of abnormal cells in a blood sample. The apparatus includes an image acquisition subsystem configured to simultaneously acquire a plurality of different types of images of individual cells in the blood sample, where the cells have been stained with a nuclear dye or stain. The plurality of different types of images exhibit morphometric and photometric parameters characteristic of the type of cell being imaged. Also included in the apparatus is a programmed image processing system for automatically identifying white blood cells in the blood sample, based on selected features derived from the morphometric and photometric parameters detected in the different types of images. The programmed image processing system uses predefined classifiers that employ the selected features for each different type of white blood cell. Any remaining cells in the blood sample that were not automatically identified as any type of white cell are designated for subsequent manual review. The manual review of the few remaining cells thus designated can readily and efficiently determine if any of the remaining cells are cancerous or abnormal. Other functions of the apparatus correspond generally to those implemented in the method discussed above.

Yet another aspect of this technology is directed to a method for determining classifiers for identifying each type of white blood cell in a sample of blood. White blood cells in a donor sample are labeled with both a nuclear dye or stain, and with monoclonal antibodies selected for identification of each type of white blood cell, producing a stained sample. The number of red blood cells in the stained sample are substantially reduced, producing a residual sample. Cells in the residual sample are processed using an imaging system that simultaneously produces a set of different types of images for each white blood cell. The set includes a bright field image, a side scatter image, an immunofluorescence image, and a nuclear fluorescence image. The immunofluorescence images are used to determine truth in regard to identifying the types of white blood cells included in the residual sample. The bright field, side scatter, and nuclear fluorescence images are analyzed to detect photometric and morphometric parameters comprising features of each type of white blood cell that was thus identified. Based on selected features detected, a classifier for each type of white blood cell is defined for use in automated identification of white blood cells labeled with the nuclear dye or stain, which are included in subsequent samples processed with the imaging system.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 7 is a listing of 370 features used for an exemplary granulocyte classifier and a graph showing how the classifier distinguishes between granulocytes (i.e., eosinophils, neutrophils, and basophils) and non-granulocytes (i.e., lymphocytes and monocytes);

Figure 3A:
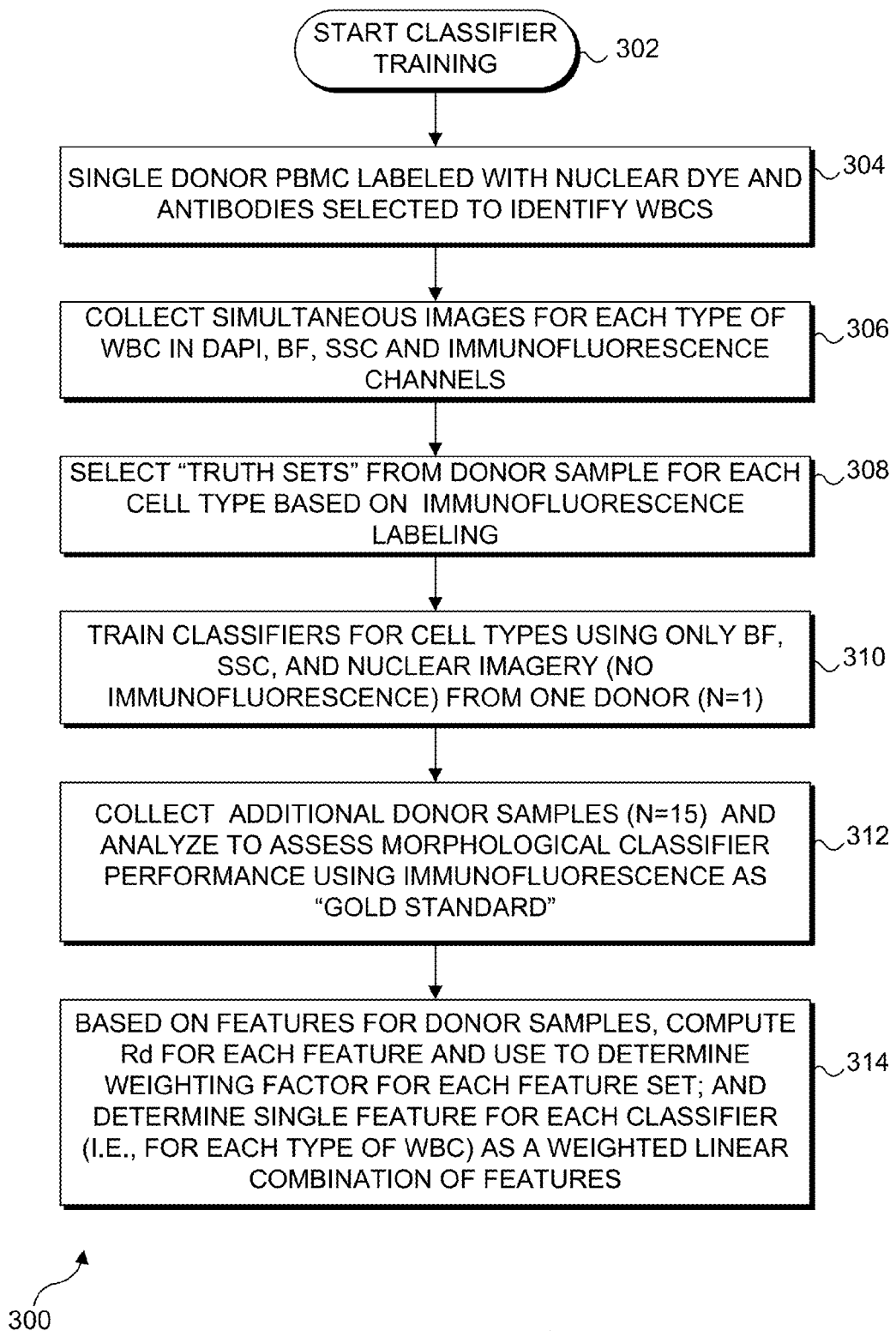
FIG. 3A is a flowchart showing exemplary logic for training a classifier for use in identifying the types of white blood cells based on features detected in images of white blood cells identified using immunofluorescence as "truth;"
Figure 3B:
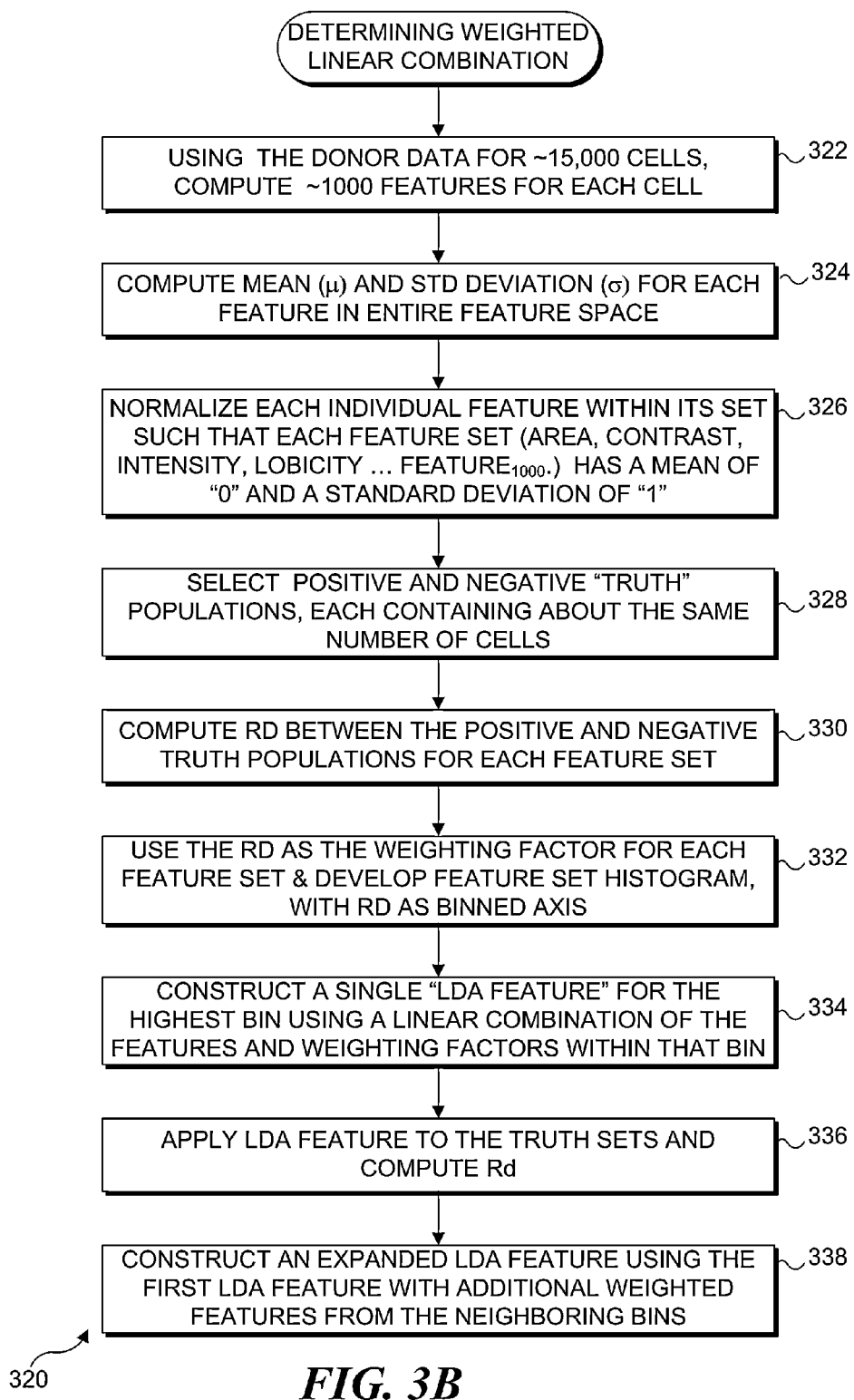
FIG. 3B is a flowchart showing exemplary logic for determining a weighted linear combination of features used for classifiers of each type of white blood cell in a sample.
Figure 3C:
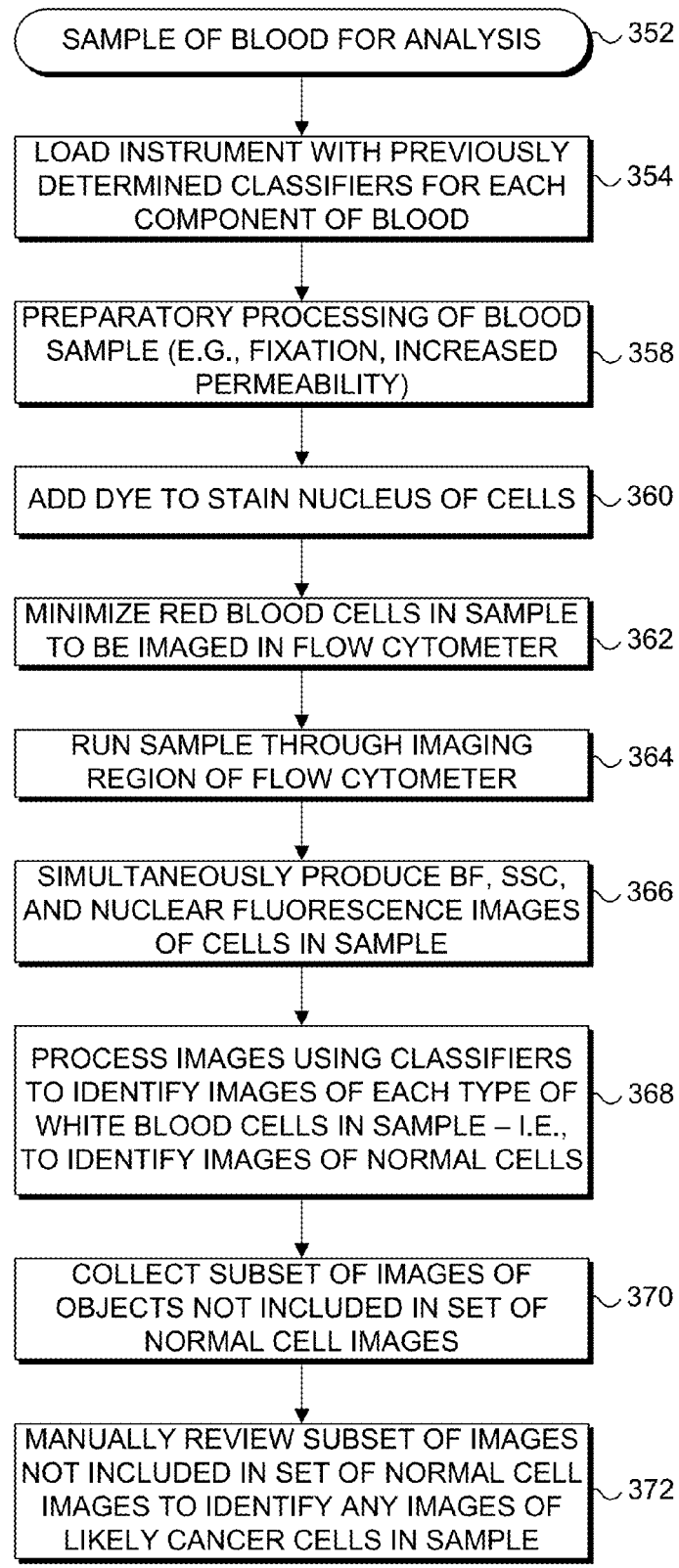
FIG. 3C is a flowchart showing exemplary logic for determining the types of white blood cells in a sample using the classifiers determined in FIGS. 3A and 3B.
Figure 12:
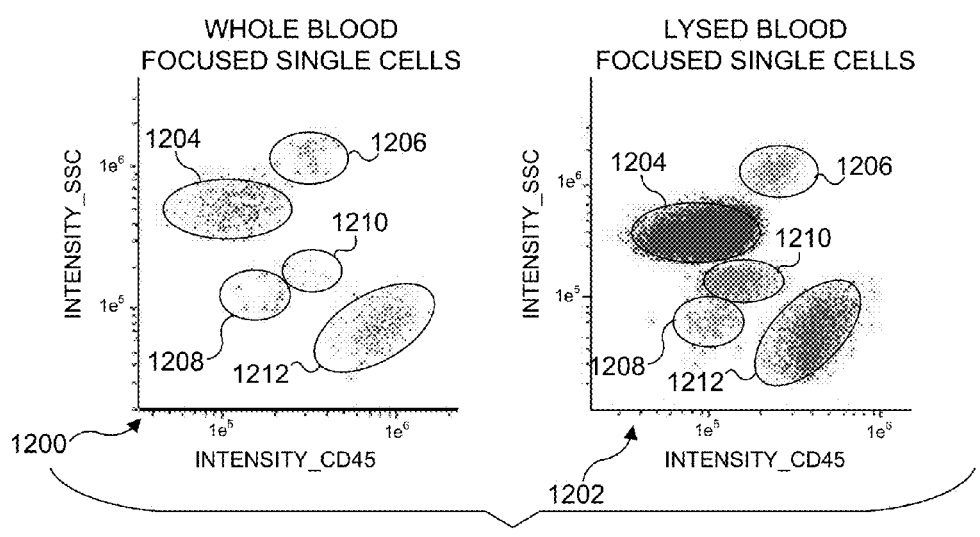
Figure 14:
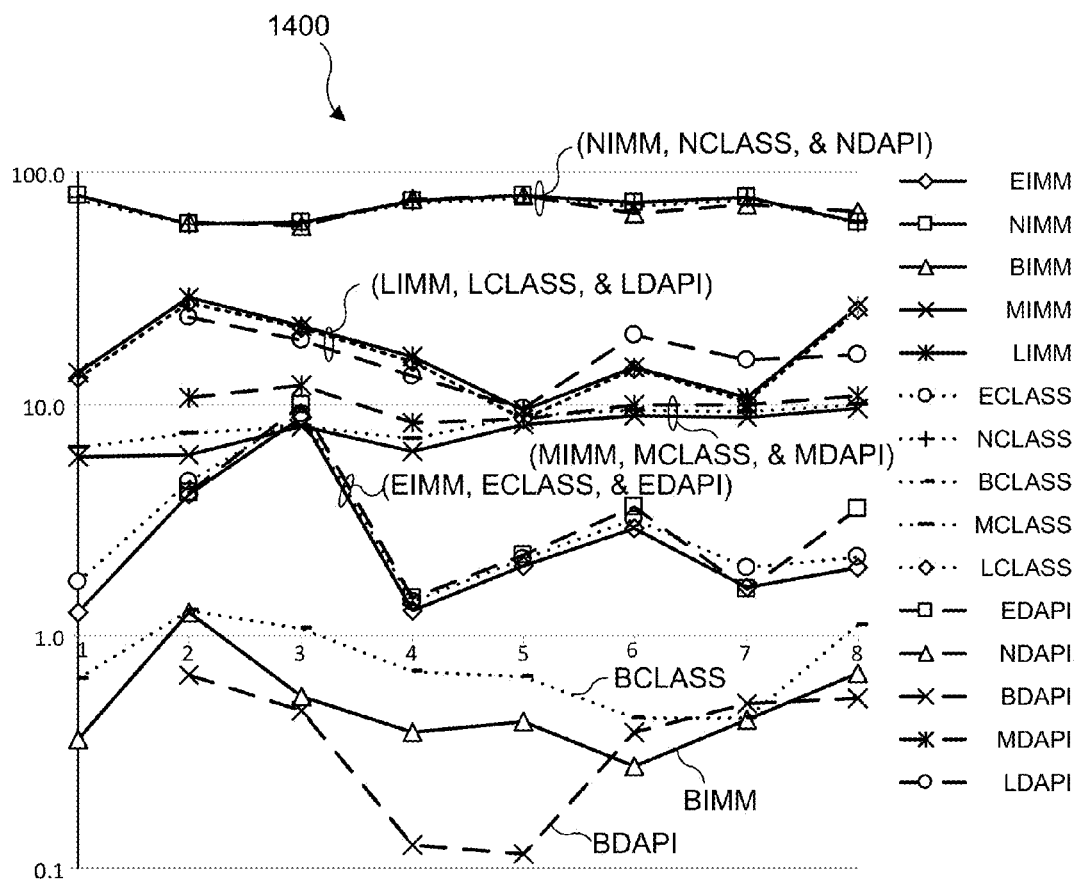
Figure 15:
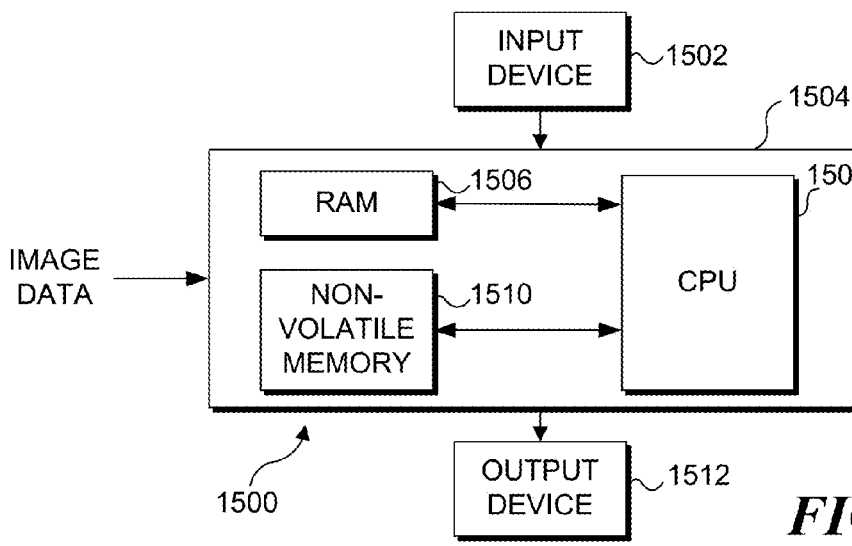

FIG. 12 includes graphs comparing the results for whole blood focused single cells (on the left) and for lysed blood focused single cells (on the right) in regard to the intensity in the immunofluorescence of CD45 and side scatter channels;

FIG. 13 illustrates equations for determining the sensitivity and specificity for classifier identifications and a table providing definitions of the terms used in the equations;

FIG. 14 is an exemplary graph illustrating the relative concentrations (log scale) of each the five types of white blood cells for eight samples, using immunofluorescence, a classifier, and a classifier on DAPI only; and FIG. 15 is a schematic block diagram of an exemplary computing system or image processing system used to implement the processing and identification of white blood cells, as noted in relevant portions of the flowcharts in FIGS. 3A, 3B, and 3C.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

With respect to the following disclosure, and the claims that follow, it should be understood that the term population of cells refers to a group of cells including a plurality of cells. Thus, a population of cells must include more than one cell.

The term multispectral images is intended to refer to images that are formed using light that has been spectrally dispersed (such as by a prism, where each different wavelength of light exits the prism at a different nominal angle) or spectrally decomposed (such as by a set of filters, where each filter emits a band of different wavelengths, such as red light, or blue light).

The term multimodal images is intended to refer to images that are formed using different types of light from a cell. Fluorescent images are formed using light emitted by the cell in response to the excitation of a fluorophore (naturally present or added to the cell). Dark field images, side scatter images, and bright field images are formed using different illumination techniques, which are well known in the field of microscopy. Thus, fluorescent images, bright field images, side scatter images, and dark field images are each formed using different imaging modes. Multimodal images must therefore include at least two images acquired using a different mode.

Classifiers are used in the following procedure to automatically identify the five types of white blood cells, based on features in images of the cells. These features include morphometric parameters, and photometric parameters, as defined below. The term morphometric parameter refers to a quantifiable parameter involving the shape, texture, and size of an object (i.e., a cell or portions of a cell). Morphometric parameters facilitate rigorous comparisons, enable complex shapes to be described in a rigorous fashion, and permit numerical comparison between different shapes (i.e., cells). By reducing shape to a series of numbers, it allows objective comparisons. When applied to different types of cells on a statistical basis, morphometric analysis can highlight specific morphometric parameters that can be used to distinguish different types of cells.

The term photometric parameter refers to a quantifiable parameter that can be directly measured from an image, such as contrast, density, and color. Exemplary photometric parameters include, but are not limited to, nuclear optical density, cytoplasm optical density, background optical density, and ratios of selected pairs of these values.

Overview

As noted above, it is possible to use an imaging system like that disclosed herein for specifically identifying cancer cells and other abnormal cells in a sample, as disclosed in other commonly owned patents and applications referenced above. However, instead of identifying cancer cells in the sample using the imaging system and automated software, the present approach identifies normal components of a sample. Any remaining objects that are not identified as being normal components can then be grouped in a subset, and the images of the objects in the subset can be manually reviewed to confirm whether they are cancerous or abnormal cells. In contrast to manually viewing all of the cells in a sample through a microscope, which might practically face a limit of about 200 cells in a session before mental/visual fatigue sets in, the present approach enables a person to view only the few images of cells in the subset that are likely to be cancerous or otherwise abnormal, since they were not automatically identified as normal components of the sample.

A peripheral blood sample that is processed in accord with the present approach will have red blood cells and white cells. Mature red blood cells do not have a nucleus, and since cancer cells and other abnormal cells of interest normally do, it is generally more efficient not to image the red blood cells when trying to define a subset of images that may be of cancerous or abnormal cells. Several different approaches can be employed to preprocess a blood sample so as to minimize the number of red blood cells that are imaged. The imaging system need only identify the five types of white blood cells in the images of the remaining portion of the sample. Any other objects or cells that are not one of the five types of white blood cells can be collected into the subset for further manual review, since such objects or cells are likely to be cancerous or otherwise abnormal.

It is desirable to simplify the process needed to identify each of the five types of white blood cells in the portion of a sample that is actually imaged. In an exemplary method, a nuclear dye or stain is applied to the cells in a sample to be processed. The cells in the sample are then processed through the imaging system to produce bright field, side scatter, and nuclear fluorescent images of each cell. Based upon classifier features previously determined using a gold standard for truth, the object in each image can be identified if it is one of the five types of white blood cells and if not identified in this manner, is placed in the subset of images of possible cancerous or abnormal objects. The images not classified as one of the five white blood cell types can be manually reviewed to confirm whether the objects in each image are cancerous or abnormal. Manual review of the few images of objects that are likely to be cancer cells or abnormal may only be required, compared to the thousands of cells that are automatically identified as one of the five types of white blood cells in a sample.

The procedure for identifying each of the white blood cells is intended to be accomplished using classifier features that have previously been determined for each type of white blood cell having DNA in the nucleus stained with only a nuclear fluorescent stain or dye. Clearly, it is important that the classifier features employed for identifying each type of white blood cell be accurate, i.e., that identification be achieved with relatively high sensitivity and high specificity to avoid false negatives and false positives, respectively. The development of the classifier features for use in connection with identifying each type of white blood cell stained with a nuclear dye need only be carried out once, and the resulting classifier features can then be employed in identifying each type of white blood cell, for all future samples from any number of different subjects.

To develop the classifier features, each donor sample used for the training procedure was stained with antibodies specific to the different types of white blood cells. Since the imaging system discussed above can simultaneously produce multiple types of images, it was used to train for classifier features in regard to the nuclear dye, based on the gold truth image determination provided by labeling the cells with the antibodies, and using bright field (BF), and side scatter (SSC), and immunofluorescence images. Thus, the images produced in response to the antibodies were used to identify each type of white cell, and the features related to the nuclear fluorescence images produced by the nuclear dye for each type white cell thus identified were used to create the classifier based on the nuclear dye images of those white cells. This process was repeated for multiple donor samples, to ensure that the classifier features are able to accurately identify the types of blood cells based only on the nuclear dye imaging and without requiring labeling the cells with monoclonal antibodies. A further step in automating the identification of the types of white blood cells makes use of linear discriminant analysis (LDA). LDA is a high dimensional technique using a weighted linear combination of features to best separate classes of objects. This approach seeks to maximize differences between classes of objects, such as the different types of white blood cells, while minimizing the differences within each class. The result is a single "feature" or classifier comprising many weighted features. The images of the cells used to develop the classifiers can be evaluated in regard to more than 1000 features. The features can be weighted based on their ability to discriminate between classes of objects, i.e., between the different types of white blood cells. By creating a linear weighted combination of these features, a specific single "feature" or classifier can be developed for each type of white blood cell, as described in greater detail below.

Overview of an Exemplary Imaging System

Figure 1A:
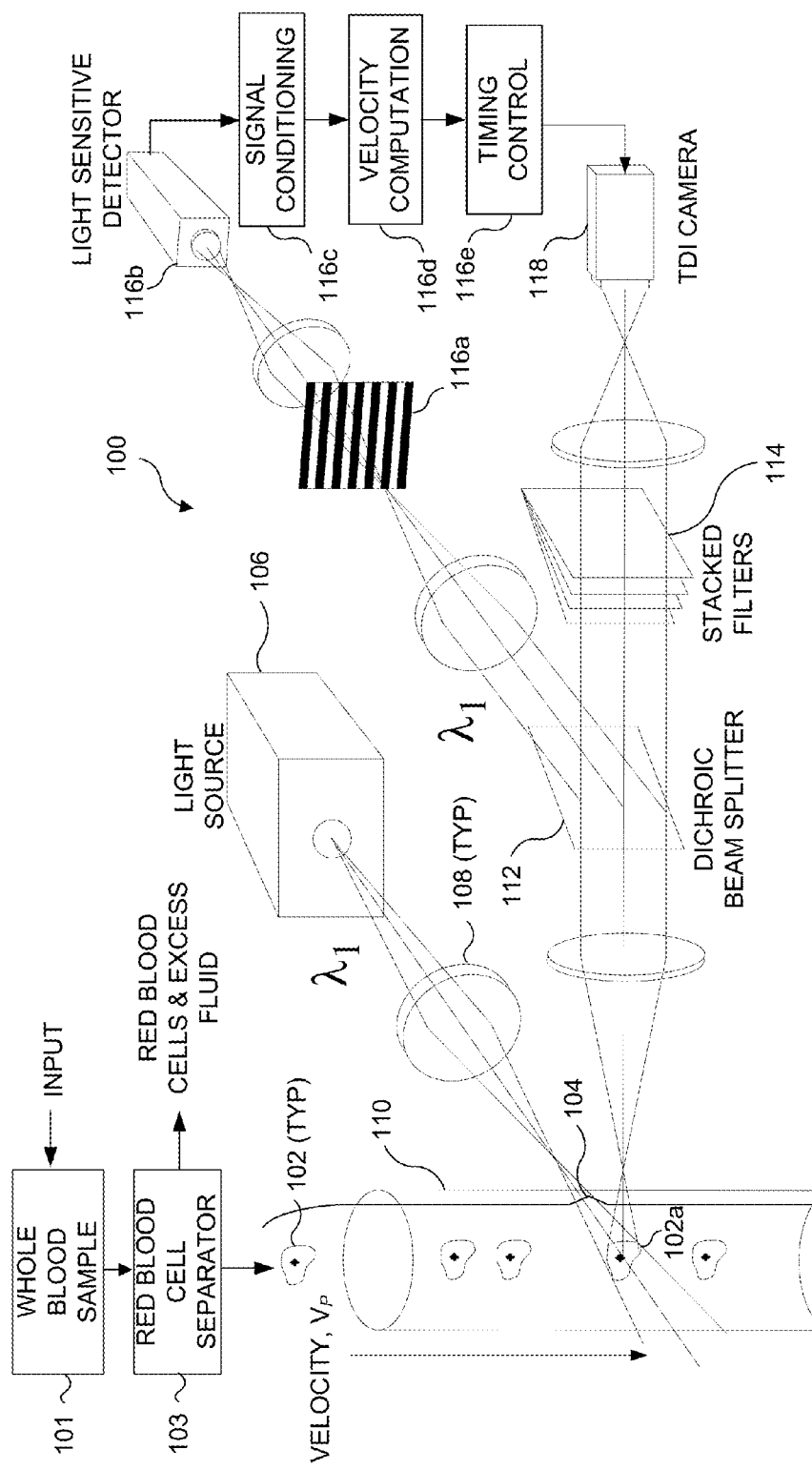
FIG. 1A is a schematic diagram of an exemplary flow imaging system that can be used to simultaneously collect a plurality of images from an object in flow, such as cells that are to be identified as one of the five types of white blood cells.

FIG. 1A is a schematic diagram of an exemplary flow imaging system 100 that uses TDI when capturing images of objects 102 (such as biological cells), entrained in a fluid flow 104 that is conveyed through an imaging region of the imaging system. In an exemplary embodiment relevant to this particular application, a whole blood sample is input to the flow imaging system and is passed through a red blood separator 101 that uses one of the techniques discussed below to separate red blood cells and excess fluid from the sample before the sample passes into the imaging region, since it is desirable to have a relatively high concentration of cells to be imaged in the flow stream to optimize the efficiency of the imaging system, and there is no need to image the red blood cells, since they cannot be cancer cells.

Imaging system 100 includes a velocity detecting subsystem that is used to synchronize a TDI imaging detector 118 with the flow of fluid through the system. Significantly, imaging system 100 is capable of simultaneously collecting a plurality of different types of images of an object. Exemplary imaging system 100 is thus configured for multi-spectral imaging and can operate, for example, with six spectral channels, including: DAPI fluorescence (400-460 nm), dark field (460-500 nm), FITC fluorescence (500-560 nm), PE fluorescence (560-595 nm), bright field (BF) (595-650 nm), and Deep Red (650-700 nm), although it will be understood that imaging system can be employed to produce still other types of images. The TDI detector in this exemplary system can provide 10 bit digital resolution per pixel. The numeric aperture (NA) of the imaging system is about 0.75, with a pixel size of approximately 0.5 microns. However, those skilled in the art will recognize that this flow imaging system is neither limited to six spectral channels, nor limited to either the stated aperture size or pixel size and resolution. For example, side scatter (SSC) images can also be simultaneously captured along with other types of images.

Moving objects 102 are illuminated using a light source 106. The light source may be a laser, a light emitting diode, a filament lamp, a gas discharge arc lamp, or other suitable light emitting source, and the imaging system may include optical conditioning elements such as lenses, apertures, and filters that are employed to deliver broadband or one or more desired relatively narrow wavelengths or wavebands of light to the object with an intensity required for detection of the velocity, and one or more other characteristics of the object based on the images that are created. Light from the object is split into two light paths by a dichroic beam splitter 112. Light traveling along one of the light paths is directed to the velocity detector subsystem, and light traveling along the other light path is directed to TDI imaging detector 118. A plurality of lenses 108 are used to direct light along the paths in a desired direction, and to focus the light. Although not shown, a filter or a set of filters can be included to deliver to the velocity detection subsystem and/or TDI imaging detector 118, only a narrow band of wavelengths of the light corresponding to, for example, the wavelengths emitted by fluorescent or phosphorescent molecules in/on the object, or light having the wavelength(s) provided by the light source 106, so that light from undesired sources is substantially eliminated at the velocity detection subsystem and/or for a given channel (type of image) at the TDI imaging detector.

The velocity detector subsystem includes an optical grating 116a that amplitude modulates light from the object, a light sensitive detector 116b (such as a photomultiplier tube or a solid-state photodetector), a signal conditioning unit 116c, a velocity computation unit 116d, and a timing control unit 116e. The signal output from the velocity detector subsystem is employed to assure that TDI imaging detector 118 is synchronized to the flow of fluid 104 through the system. Optical grating 116a preferably comprises a plurality of alternating transparent and opaque bars that modulate the light received from the object, producing modulated light having a frequency of modulation that corresponds to the velocity of the object from which the light was received, as the object travels along the flow path through the imaging system. The optical magnification and the ruling pitch of the optical grating can be chosen such that the widths of the bars are approximately the size of the objects being illuminated, e.g., so that the width of the bars is about equal to the diameter of objects such as cells that are being imaged. Thus, the light collected from cells or other objects is alternately blocked and transmitted through the ruling of the optical grating as the objects traverse the interrogation region, i.e., the field of view. The modulated light is directed toward a light sensitive detector, producing a signal that can be analyzed by a processor to determine the velocity of the objects. The velocity measurement subsystem is used to provide timing signals to TDI imaging detector 118 for purposes of achieving the above-noted synchronization.

Signal conditioning unit 116c can comprise a programmable computing device, although an application specific integrated circuit (ASIC), other logic hardware, or a digital oscilloscope can also be used for this purpose. The frequency of the photodetector signal is measured, and the velocity of the object is computed as a function of that frequency. The velocity dependent signal is periodically delivered to timing control unit 116e to adjust the clock rate of TDI imaging detector 118. Those of ordinary skill in the art will recognize that the TDI detector clock rate is adjusted to match the velocity of the image of the object as the image moves over the TDI detector to within a small tolerance selected to ensure that longitudinal image smearing in the output signal of the TDI detector is within acceptable limits. The velocity update rate must occur frequently enough to keep the clock frequency within the tolerance band as flow (object) velocity varies.

Beam splitter 112 is employed to divert a portion of light from an object 102a to light sensitive detector 116b, and a portion of light from object 102a to TDI imaging detector 118. In the light path directed toward TDI imaging detector 118, there is a plurality of stacked dichroic filters 114, which separate light from object 102a into a plurality of wavelengths. One of lenses 108 is used to form an image of object 102a on TDI imaging detector 118.

The theory of operation of a TDI detector like that employed in imaging system 100 is as follows. As objects travel through a flow tube 110 (FIG. 1A) and pass through the volume imaged by the TDI detector, light from the objects forms images of the objects, and these images travel across the face of the TDI detector. The TDI detector can comprise a charge coupled device (CCD) array, which is specially designed to allow charge to be transferred on each clock cycle, in a row-by-row format, so that a given line of charge remains locked to, or synchronized with, a line in the image. The row of charge is clocked out of the array and into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great benefit in a detector intended to respond to images from low-level fluorescence emission of an object and other low light levels received from the object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the concepts disclosed herein use an accurate estimate of the object's velocity, and thus, of the velocity of the image as it moves over the CCD array of the TDI detector. A flow imaging system of this type is disclosed in commonly assigned U.S. Pat. No. 6,249,341, the complete disclosure, specification, and drawings of which are hereby specifically incorporated herein by reference.

In an exemplary implementation, cells are hydrodynamically or acoustically focused into a single-file line in a fluidic system, which can be included as part of red blood cell separator 103, forming a tall but narrow field of view as the cells flow through the region where they are imaged. This technique enables the lateral dimension of the detector to be used for signal decomposition. This aspect of this imaging system can be readily visualized with reference to FIG. 1B. Cells 132 are hydrodynamically or acoustically focused in a flow of fluid directed into a flow cuvette 130 and illuminated from one or more sides using light sources 154 and 134. This process can be included in the red blood cell separator in FIG. 1A. Light is collected from the cells with a high NA objective lens 138, and the light that is collected is directed along a light path including lenses 142a and 142b, and a slit 143. A fraction of this collected light is transmitted to an auto-focus subsystem 144 and to a velocity detection system 146. It should be noted that in connection with an imaging system that uses a TDI detector, it is important to ensure the data signal produced by the detection system, which is integrated over time to increase the signal-to-noise ratio, is properly synchronized with the flow of cells through the imaging system.

Figure 1B:
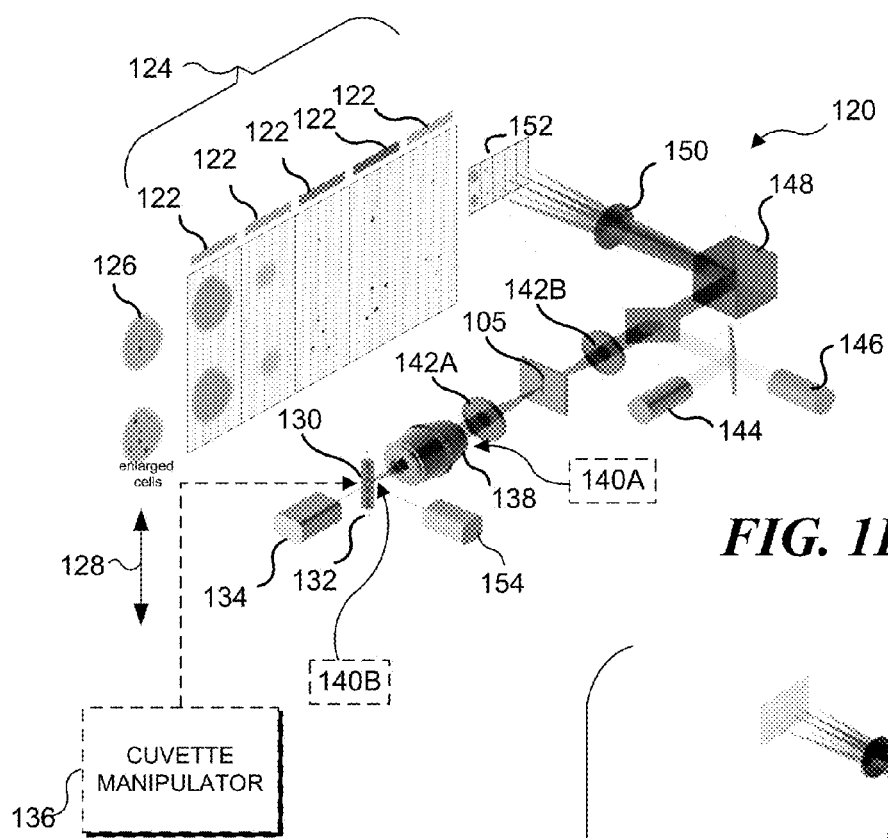
FIG. 1B is another illustration of an exemplary flow imaging system for implementing the concepts disclosed herein.

Optional distortion elements can be included in the flow imaging system, to alter the optical wave front of light from the cells in a deterministic way. The combination of a modified wave front and post-processing of the imagery enables extended depth of field (EDF) images to be obtained by the imaging system. Either an optical distortion element 140a can be disposed between the objects being imaged and the collection lens, or an optical distortion element 140b can be disposed in infinite space (that is, at the objective aperture or at a conjugate image of the aperture at a subsequent location in the optical system, but before the detector). Alternatively, optical distortion may be introduced via adjustment of a correction collar (not separately identified) on an adjustable implementation of objective lens 138. Only one means of introducing optical distortion is used. The function of the optical distortion is to change the light from the object to achieve a point spread function (PSF) that is substantially invariant across an EDF, such that negative effects of the distortion produced by the element can subsequently be removed by signal processing, to yield an EDF image. Another technique that can be used to introduce optical distortion into light from the object is to use a cuvette/flow cell having different optical thicknesses at different locations, such that imaging through the different locations of the cuvette induces different degrees of wave front deformation. For example, different faces of the cuvette can induce different levels of distortion, with one or more faces introducing no intentional distortion/deformation, with other faces configured to intentionally deform the optical wave front of light from the object. Moving the cuvette relative to the imaging optical system enables the deformation to be selectively induced. An optional cuvette manipulator 136 for manipulating the position of the cuvette relative to the optical system is shown in FIG. 1B. Where different faces of the cuvette induce different levels of deformation, such means will generally rotate the cuvette. It should also be recognized that a single face of a cuvette can induce different levels of deformation at different locations, such that translating the cuvette linearly can induce different levels of deformation. In such an embodiment, manipulator 136 will be configured to translate the cuvette linearly. Those of ordinary skill in the art will recognize that many different structural configurations can be used to implement manipulator 136, such as stepper motors, linear actuators, hydraulics, powered hinges, powered linkages, and others. The specific configuration is not critical, so long as manipulation of the cuvette does not introduce additional optical errors beyond the intentional deformation; thus, the specified structures for manipulator 136 should be considered exemplary, rather than limiting.

The majority of the light is passed to a spectral decomposition element 148, which employs a fan-configuration of dichroic mirrors 150 to direct different spectral bands laterally onto different regions of a TDI detector 152. Thus, the imaging system is able to decompose the image of a single cell 126 into multiple sub-images 122 across TDI detector 152, each sub-image corresponding to a different spectral component. In this view, TDI detector 152 has been enlarged and is shown separately to highlight its elements. Note that the different spectral or sub images are dispersed across the detector orthogonally relative to a direction of motion of the images across the detector, where that direction is indicated by an arrow 128.

Figure 1C:
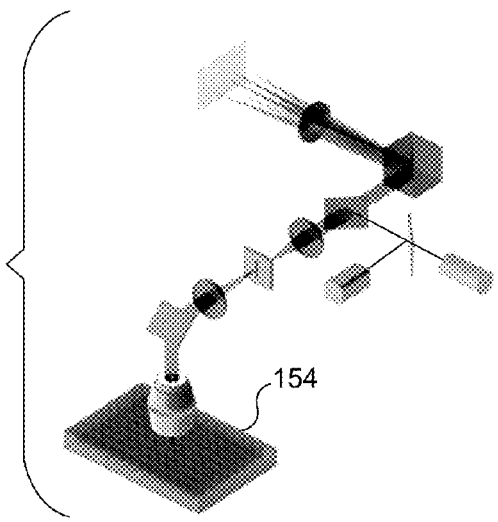
FIG. 1C is a schematic illustration of an exemplary imaging system for implementing the concepts disclosed herein, wherein the cells to be imaged are disposed on a plate or slide.

Spectral decomposition greatly facilitates the location, identification, and quantification of different fluorescence-labeled biomolecules within a cell by isolating probe signals from each other, and from background auto fluorescence. Spectral decomposition also enables simultaneous multi-mode imaging (bright field, dark field, etc.) using band-limited light in channels separate from those used for fluorescence imaging. FIG. 1B illustrates an exemplary flow-based embodiment of flow imaging system 120. However, it should be recognized that such an imaging system can be configured to collect images of objects on a plate or slide 154, where the plate/slide moves relative to the imaging system, instead of the flow-based embodiment, as indicated in FIG. 1C.

It should be recognized that other elements (such as a prism or a filter stack) could be similarly employed to spectrally disperse the light, and the dichroic mirrors simply represent an exemplary implementation. Flow imaging system 150 can employ a prism (not shown) or a grating oriented to disperse light laterally with regard to the axis of flow prior to the final focusing optics, for spectral analysis of each object's intrinsic fluorescence. In yet another exemplary embodiment of a suitable flow imaging system that is contemplated (but not shown), a cylindrical final focusing lens can be employed to image a Fourier plane on the detector in the cross-flow axis, enabling analysis of the light scatter angle. These techniques for multi-spectral imaging, flow spectroscopy, and Fourier plane scatter angle analysis can be employed simultaneously by splitting the collected light into separate collection paths, with appropriate optics in each light path. For enhanced morphology or to analyze forward scatter light, a second imaging objective and collection train can be used to image the particles through an orthogonal facet of the flow cuvette 130 (FIG. 1B), thereby viewing the objects in stereoscopic perspective with no loss of speed or sensitivity.

To analyze the collected imagery, a software based image analysis program can be employed. One example of suitable image analysis software is the IDEAS™ package (available from Amnis Corporation, Seattle, Wash.). The IDEAS™ software package evaluates over 200 quantitative features for every cell, including multiple morphologic and fluorescence intensity measurements, which can be used to define and characterize cell populations in terms of parameters or features, as discussed hereinbelow. The IDEAS™ software package enables the user to define biologically relevant cell subpopulations, and analyze subpopulations using standard cytometry analyses, such as gating and backgating. It should be understood, however, that other image analysis methods or software packages can be employed to apply the concepts disclosed herein, and the IDEAS™ image analysis software package is intended to be merely one example of a software suitable for this purpose, rather than limiting on the concepts disclosed herein.

Figure 1D:
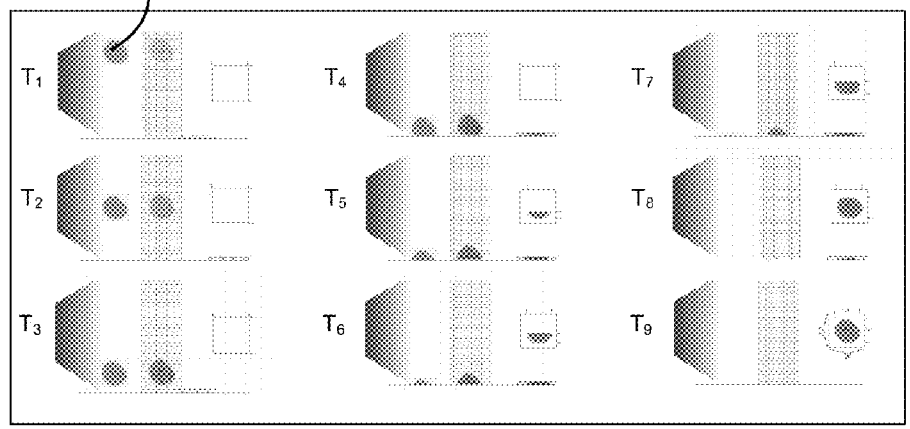
FIG. 1D is a schematic illustration of a readout provided by a time-delay integration (TDI) detector employed in an exemplary flow imaging system used in accord with the concepts disclosed herein.

Turning now to FIG. 1D, TDI detector 152 of the exemplary flow imaging system shown in FIG. 1B is implemented using TDI to perform high throughput imaging with high sensitivity. As shown in an exemplary readout 160, the image on the TDI detector is read out one row of pixels at a time, from the bottom of the TDI detector. After each row is read out, the signals in the remaining detector pixels are shifted down by one row. The readout/shift process repeats continuously, causing latent image 162 to translate down the detector during readout (note the movement of latent image 162 through frames $T_1$-$T_9$). If the readout rate of the TDI detector is matched to the velocity of the object being imaged, the image does not blur as it moves down the TDI detector. In effect, the TDI detector electronically "pans" the rate at which rows are read out to track the motion of an object being imaged. To provide optimum results for this technique, it is important to accurately measure the velocity of the objects being imaged and to employ that measurement in feedback control of the TDI readout rate. Thus, accurate velocity detection for objects moving in flow enables the TDI imaging to be implemented properly.

One significant advantage of TDI detection over other methods is the greatly increased image integration period it provides. An exemplary flow imaging system useful in connection with the present approach includes a TDI detector that has 512 rows of pixels, providing a commensurate 512 times increase in signal integration time. This increase enables the detection of even faint fluorescent probes within cell images and intrinsic auto fluorescence of cells acquired at a high-throughput.

Furthermore, the use of a TDI detector increases measured signal intensities up to a thousand fold, representing over a 30-fold improvement in the signal-to-noise ratio compared to other methods disclosed in the prior art. This increased signal intensity enables individual particles to be optically addressed, providing high-resolution measurement of either scattered spectral intensity of white light or scattered angular analysis of monochromatic light of selected wavelengths.

Exemplary flow imaging system 120 can be configured for multi-spectral imaging and can operate with six spectral channels, for example: DAPI fluorescence (400-460 nm), dark field (460-500 nm), FITC fluorescence (500-560 nm), PE fluorescence (560-595 nm), bright field (595-650 nm), and deep red (650-700 nm). The TDI detector can provide 10 bit digital resolution per pixel. The numerical aperture (NA) of the exemplary imaging system is typically about 0.75, with a pixel size of approximately 0.5 microns. However, those skilled in the art will recognize that this flow imaging system is neither limited to six spectral channels nor limited to either the stated NA, or pixel size and resolution. This system can determine well more than 1000 features/cell, which greatly facilitates the development of classifiers to identify objects. Further, the system can process more than 50,000 images/sec., so the throughput enables many cells to be imaged in multiple channels in a very short time, at a very low cost.

Figure 2:
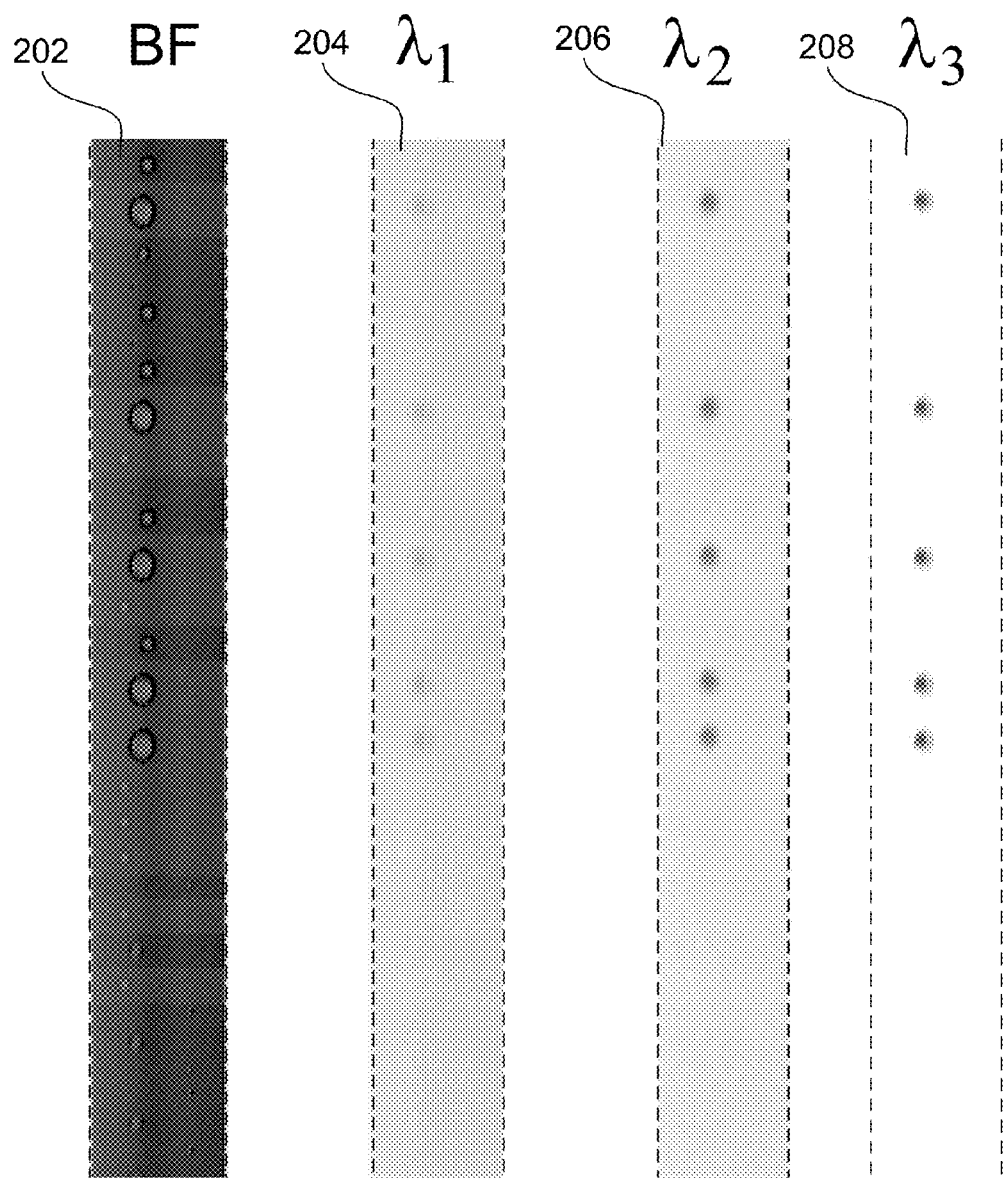
FIG. 2 is a pictorial representation of an image that might be recorded by any of the flow imaging systems of FIGS. 1A-1C.

FIG. 2 is a pictorial representation of images produced by the exemplary flow imaging systems of FIGS. 1A-1C. It should be recognized that while FIG. 2 is based on a full color image, that image has been manipulated to facilitate reproduction. The colors in the original image were reversed (i.e., a negative of the original image was obtained), then that negative was converted from a color image to a grayscale image, and contrast adjustments were performed. Thus, FIG. 2 is provided to indicate the types of cellular images that can be acquired, as opposed to faithfully reproducing actual cellular images in their original form. A column 202, labeled "BF," includes images created by the absorption of light from light source 106 (FIG. 1A) by spherical objects 102 entrained in fluid flow 104. The "BF" label refers to "bright field," a term derived from a method for creating contrast in an image whereby light is passed through a region and the absorption of light by objects in the region produces dark areas in the image. The background field is thus bright, while the objects are dark in this image. Thus, column 202 is the "bright field channel" in this example. It should be understood that the inclusion of a bright field image is exemplary, rather than limiting on the scope of the concepts disclosed herein. The concepts disclosed herein for determining classifiers for objects such as white blood cells can use a combination of bright field and/or dark field, and/or side scatter images, and fluorescent channel images.

The remaining three columns 204, 206, and 208 shown in FIG. 2 are respectively labeled "λ1," "λ2," and "λ3." These columns include images produced using light that has been emitted by an object entrained in the fluid flow. Such light can be emitted through the process of fluorescence (as opposed to images produced using transmitted or reflected light). As those of ordinary skill in the art will recognize, fluorescence is the emission of light (or other electromagnetic radiation) by a substance that has been stimulated by the absorption of incident radiation. Generally, fluorescence persists only for as long as the stimulating radiation persists. Many substances (particularly fluorescent dyes) can be identified based on the spectrum of the light that is produced when they fluoresce. Columns 204, 206, and 208 are thus referred to as "fluorescence channels." Such fluorescence can be produced by dyes or stains applied and absorbed by the nucleus of cells before the cells pass with the fluid flow through the imaging instrument, as further discussed below.

As noted above, additional exemplary flow imaging systems are disclosed in commonly assigned U.S. Pat. No. 6,211,955 and U.S. Pat. No. 6,608,682, the complete disclosure, specification, and drawings of which are hereby specifically incorporated herein by reference as background material. The imaging systems described above and in these two patents in detail, and incorporated herein by reference, have substantial advantages over more conventional systems employed for the acquisition of images of biological cell populations. These advantages arise from the use in several of the imaging systems of an optical dispersion system, in combination with a TDI detector that produces an output signal in response to the images of cells and other objects that are directed onto the TDI detector. Significantly, multiple images of a single object can be collected at one time. The image of each object can be spectrally decomposed to discriminate object features by absorption, scatter, reflection, or emissions, using a common TDI detector for the analysis. Other systems include a plurality of detectors, each dedicated to a single spectral channel.

These imaging systems can be employed to determine morphological, photometric, and spectral characteristics of cells and other objects by measuring optical signals including light scatter, reflection, absorption, fluorescence, phosphorescence, luminescence, etc. Morphological parameters include area, perimeter, texture or spatial frequency content, centroid position, shape (i.e., round, elliptical, barbell-shaped, etc.), volume, and ratios of selected pairs (or subsets) of these parameters. Similar parameters can also be determined for the nuclei, cytoplasm, or other sub-compartments of cells with the concepts disclosed herein. Photometric measurements with the preferred imaging system enable the determination of nuclear optical density, cytoplasm optical density, background optical density, and ratios of selected pairs of these values. An object being imaged with the concepts disclosed herein can either be stimulated into fluorescence or phosphorescence to emit light, or may be luminescent, producing light without stimulation. In each case, the light from the object is imaged on the TDI detector to use the concepts disclosed herein to determine the presence and amplitude of the emitted light, the number of discrete positions in a cell or other object from which the light signal(s) originate(s), the relative placement of the signal sources, and the color (wavelength or waveband) of the light emitted at each position in the object, the shape of components in the object, such as a nucleus, and many other features. Literally a thousand or more features useful for identifying specific types of cells or objects in cells can be derived from images produced by an imaging system like that described above. With appropriate software to analyze the images thus produced, it is possible to determine the type of cells flowing through the imaging instrument at a relatively rapid rate, which is an important benefit of the present approach.

Details of Project to Develop Classifiers for White Blood Cells

In Stage 1 of the project, a dozen samples of blood were collected from normal human donors. The blood was stained with a fluorochrome conjugated anti-CD45 monoclonal antibody, and then the red blood cells (RBCs) in the samples were lysed. Imagery was acquired on the resultant peripheral white blood cells after formalin fixation, permeabilization with Triton X-100 (0.1%), and staining with the nuclear dye 4',6-diamidino-2-phenylindole (DAPI). The intensity of CD45 expression and cell SSC were used to identify the five sub-populations of peripheral white blood cells (WBCs) and to establish the "truth" regarding the type of white blood cell being imaged. Classifiers were then trained using a few hundred BF, SSC and DAPI images from each "truth" population from a donor sample and were applied to the remaining samples. The classification was performed in two steps. First, granulocytes (eosinophils, neutrophils and basophils) were identified and distinguished from non-granulocytes (monocytes and lymphocytes). In the second step, the five individual sub-populations from the resulting populations of the first step were identified to obtain a five-part differential. Using this process, >90% sensitivity was obtained for eosinophils, neutrophils, and lymphocytes; but, the process performed poorly on monocytes (60%) and basophils (<5%). However, the process achieved >90% specificity for all five sub-populations of white blood cells.

Close examination of the results and the image data revealed that the monocytes and basophils suffered from not having well-established "truth" populations. The CD45 expression that was used to denote "truth" was not always valid. In order to get more reliable "truth" determinations for training the classifiers and for establishing performance metrics, it was decided to incorporate immunofluorescence staining specifically for monocytes and basophils into the protocol and to use these as "truth" to determine if the performance (sensitivity) improved.

Stage 2 of the project involved trying to improve on the results obtained in the first stage. Towards this end, an anti-CD14 monoclonal antibody was used to stain for the monocytes, and the cells with high CD14 expression were identified as "true" monocytes (both for the training set from one file, and for sensitivity and specificity performance metric computations in all data files). This approach improved the monocyte sensitivity to >90%. In stage 3, anti-CD123 and anti-CD193 monoclonal antibodies were used to stain for basophils (because basophils are uniquely positive for both markers) in addition to staining for monocytes (using anti-CD14). Large data sets were collected using more donor samples, to ensure that a statistically significant number of basophils were included for quantification. In addition, the classifiers were retrained to identify each sub-population separately (E versus (basophils and neutrophils), neutrophils versus monocytes, monocytes versus lymphocytes, basophils versus lymphocytes). This strategy was tested on eight data files, resulting in an improvement over the earlier results to about 75% sensitivity on basophils, while maintaining the >90% sensitivity on the remaining sub-populations and >90% specificity across all five sub-populations. For these donor samples, data files were also acquired with WBCs stained only with the nuclear dye DAPI, and the results of the relative percentage of each sub-population in these samples were compared to those obtained from the same donor with the CD45, CD14, CD123 and CD193 stains. There were some discrepancies in the results (especially, for basophils) that warranted closer examination. To improve the results, the staining and classification strategy was repeated across sample from even more donors with multiple repeats of each donor, which helped to determine if a consistent pattern existed to improve the quality of the classifiers. The purpose of testing the classifiers on DAPI-only (i.e., nuclear stained-only) stained samples is to ensure that results achieved on data with population-specific staining can be reproduced on data from the same donor with nuclear stain-only staining, since use of the feature sets of classifiers to identify the white blood cells associated with a nuclear stain such as DAPI will thereafter be used by the imaging system in the automated identification of images of the five types of white blood cells during the analysis of samples of patient blood, as described below. Examples of other types of nuclear (DNA) fluorescent dyes or stains that might be used include cell-permeant cyanine nucleic acid stains, such as SYTO™ dyes (available from Molecular Probes), an A-T intercalating anthraquinone stain, such as DRAQ5™ (available from BioStatus), 7-Aminoactinomycin D (7-AAD), and propidium iodide (PI), to name a few examples and without any intended limitation. The feature sets for the classifiers used with nuclear stain or dyes are based on imaging the cells with the imaging system, to produce bright field, side scatter, and nuclear fluorescence images of each cell.

As noted above, more than 1000 features can be derived from the bright field, side scatter, and nuclear fluorescence images of an object. Some of these features are more useful in grouping white blood cells of the same type together, and for separating white blood cells of different types from each other. Based upon the use of truth sets determined by imaging during the initial classifier training that was done with donor blood samples, it is possible to rank the efficacy of different features for use in classifying each type of white blood cell. In other words, an ultimate classifier for a given one of the five types of white blood cells might contain hundreds of individual weighted features or just a few. These features that are used for a classifier may include criteria such nuclear area, NC ratio, number of lobes in the nucleus, the circularity of the nucleus, cell size, scatter intensity, etc. The following approach thus applies weighting to take into consideration the relative importance of each of the more than 1000 features evaluated with the initial donor samples, when determining a single classifier feature that is a linear combination of many weighted features.

FIG. 3A illustrates exemplary steps that can be employed to develop the classifiers used to enable the imaging system to automatically recognize each type of white blood cell based on images produced of the white blood cells that have been stained with a nuclear dye, such as DAPI. A start block 302 indicates that the procedure implements classifier training. In a block 304, the peripheral blood mononuclear cells from a single donor are labeled with a nuclear dye, one example of which is DAPI, and with antibodies that are selected to enable accurate identification of the five different types of white blood cells. The stains used in the exemplary procedure were fluorochrome conjugated anti-CD45, anti-CD14, anti-CD123 and anti-CD193 monoclonal antibodies; however, it will be understood that these specific stains are exemplary and are not intended to be limiting, since other stains might instead be used. The anti-CD14 monoclonal antibody is included to more accurately identify monocytes, since the cells with high CD14 expression can readily identified as "true" monocytes. Similarly, both anti-CD123 and anti-CD193 are used to stain for basophils, since basophils are uniquely positive for both of these markers. The anti-CD45 monoclonal antibody is used for accurately identifying eosinophils, neutrophils, and lymphocytes.

A block 306 provides for simultaneously collecting images for each type of white blood cells in the DAPI (nuclear fluorescence), side scatter, and immunofluorescence imaging channels of the imaging system. The immunofluorescence channels provide the "truth" of the type of each white blood cell being imaged, as indicated in a block 308. As noted in a block 310, the classifiers for each type of white blood cell can be "trained" using features derived from the bright field, side scatter, and nuclear fluorescence (DAPI) channel images for a white blood cell type identified based on the immunofluorescence channel images. To improve the quality of the classifier features, a block 312 provides for collecting additional donor samples, e.g., 15 more samples from different donors and analyzing the samples with the imaging system to assess morphological classifier performance, again using the immunofluorescence criteria as the "gold standard" to identify the type of white blood cell being imaged.

In a block 314, a value of the discrimination ratio, $R_d$, is computed for each feature and is used to determine a weighting factor for each feature in a set of features for a given type of white blood cell. The weighting factor is then used to determine a weighted linear combination of features for that type of white blood cell.

Details of the process for determining the weighted linear combination are illustrated in an exemplary flow chart in FIG. 3B. A block 322 indicates the donor imagery data for thousands of white blood cells, i.e., about 15,000 in this example, are used to compute or determine more than 1000 different features for each type of white blood cell. In the indicated example, the result is over 15 million feature values. It will be understood that the type of white blood cell associated with each feature set is based on the "truth" provided by the immunofluorescence images, as discussed above. In a block 324, the mean, $\mu$, and standard deviation, $\sigma$, are computed for each feature in the entire feature space, yielding more than 1000 values for $\mu$ and more than 1000 values for $\sigma$. A block 326 normalizes each individual feature within its set such that each feature set (e.g., area, contrast, intensity, lobicity, . . . feature$_{1000}$) has a mean equal to 0 and a standard deviation equal to 1. For example, a normalized feature for area, area$_{1n}$, is computed as follows:

$$\text{area}_{1n} = (\text{area}_1 - \mu_{area})/\sigma_{area}. \quad (1)$$

This normalization provides a normalized standard that is used for comparing the discrimination power of each feature, e.g., area, in regard to use in identifying a specific type of white blood cell.

Figure 4:
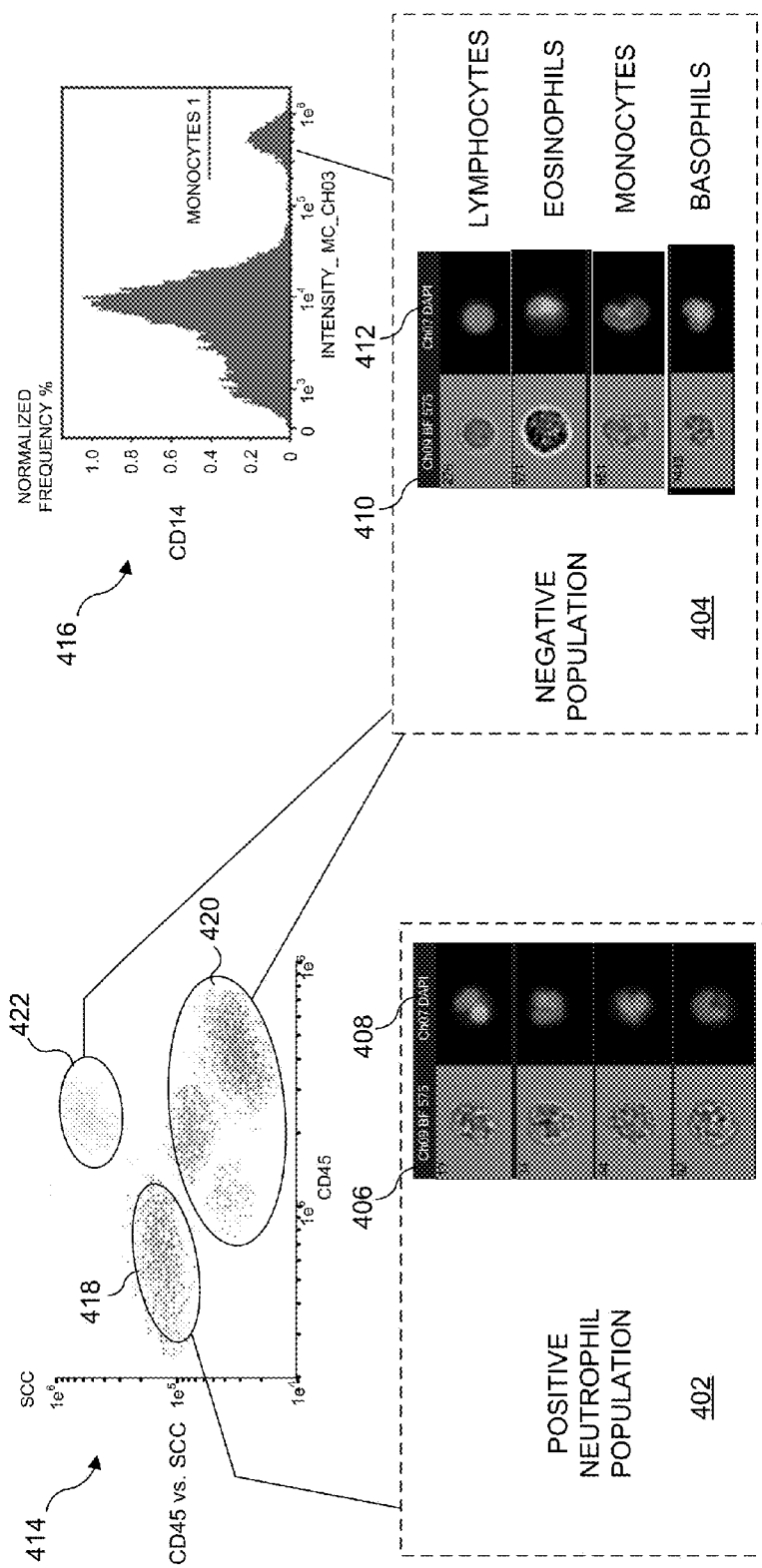
FIG. 4 illustrates images and graphs providing an example of positive and negative "truth" populations in regard to neutrophils, for an immunofluorescence channel for CD45 vs. a side scatter channel.

In a block 328, a positive truth population and a negative truth population are selected for each type of white blood cell, and each contains about the same number of cells. An example 400 is illustrated in FIG. 4. In this example, a positive neutrophil population 402 is illustrated in regard to an immunofluorescence channel for CD45, and a side scatter channel in a graph 414. In graph 414, the neutrophils are generally encompassed by an ellipse 418, and the non-neutrophils (i.e., negative population of the other four types of white blood cells) are generally encompassed by ellipses 420 and 422. Bright field images and the DAPI images are illustrated in columns 406 and 408 for four neutrophil cells. A negative population 404 of non-neutrophil cells, i.e., of lymphocytes, eosinophils, monocytes, and basophils are each shown in bright field images and DAPI images in columns 410 and 412, respectively. Also included is a graph 416 of the normalized frequency for the CD14 immunofluorescence light relative to the intensity of the light in channel 3, which is used for monocytes truth detection.

Figure 5A:
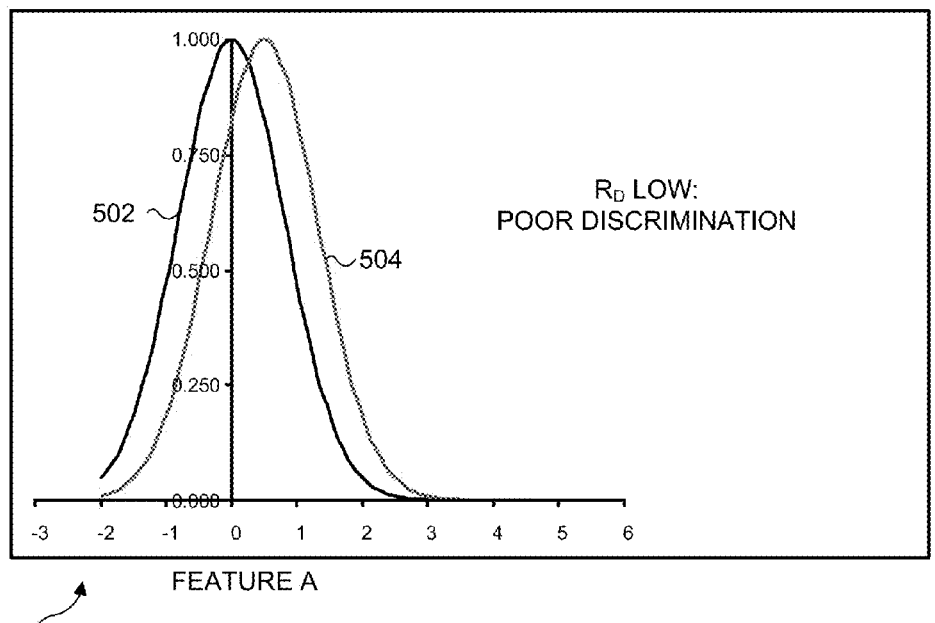
FIGS. 5A and 5B are respectively graphs showing examples of poor discrimination (low discrimination ratio, $R_d$) for a feature A, and good discrimination (high $R_d$) for a feature B.
Figure 5B:
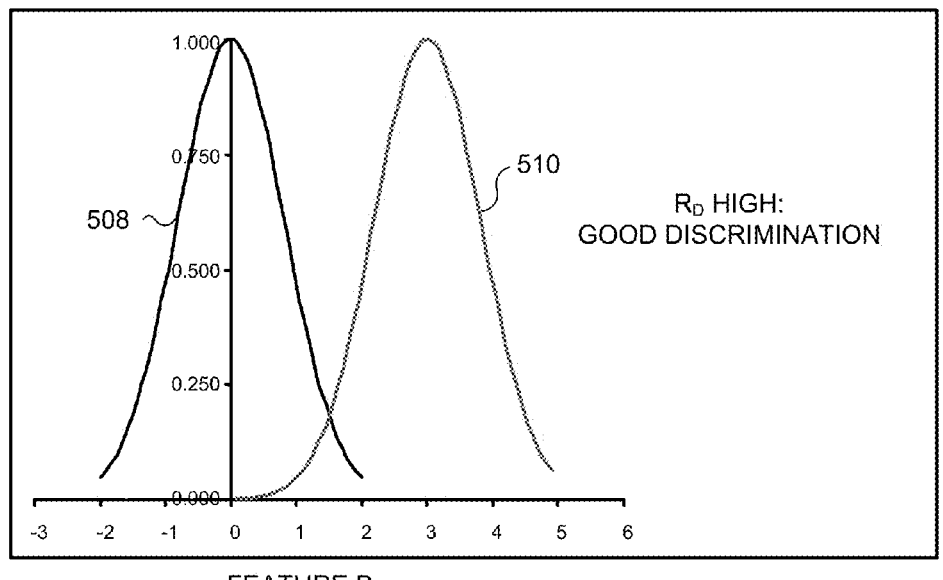
Figure 6A:
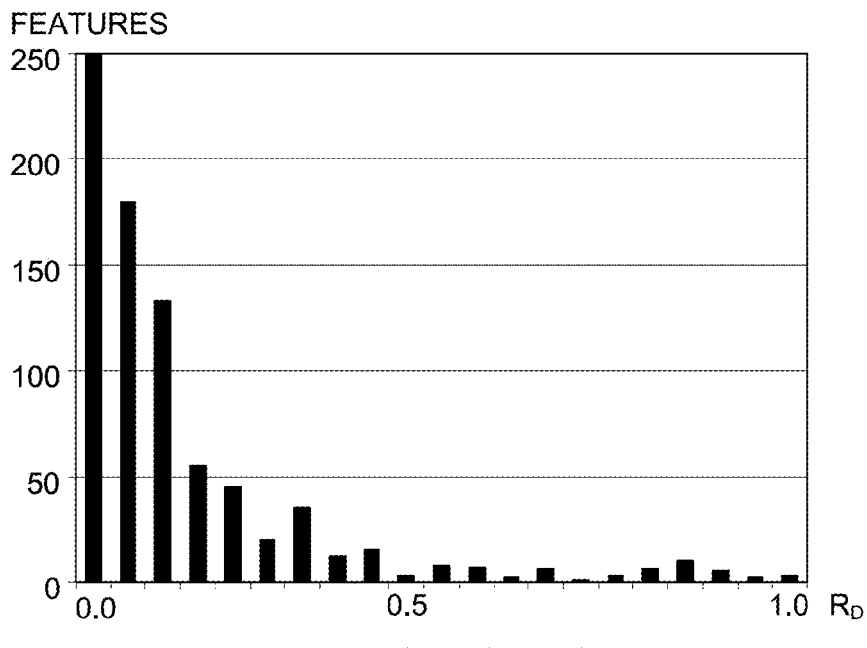
FIG. 6A is an exemplary feature set histogram relative to $R_d$.

Referring back to FIG. 3B, a block 330 provides for computing the discrimination ratio, $R_d$, between the positive and negative truth populations for each feature set. Thus, each truth population would include about 1000 values for $R_d$. An example of a feature A for which the value of $R_d$ is low is illustrated in a graph 500 in FIG. 5A. A curve 502 for the positive population for that feature is not very well separated from a curve 504 for the negative population for that feature, showing that this feature yields a relatively poor discrimination between the positive and negative populations of types of white blood cells. In contrast, a graph 506 shows that for a feature B, the value of $R_d$ is high and thus, there is good discrimination between a positive population curve 508 and a negative population curve 510. Therefore, feature B is very useful in distinguishing between a specific type of white blood cell and all of the other types of white blood cells (or other objects). Accordingly, a block 332 in FIG. 3B provides for using the value of $R_d$ as a weighting factor for each feature set and for developing a feature set histogram, with $R_d$ as the binned axis. An example of such a histogram 600 is illustrated in FIG. 6A, in regard to 250 features. Features with the greatest discrimination, i.e., largest value of $R_d$, appear on the right side of the histogram and those with the least amount of discrimination appear on the left side.

A block 334 in FIG. 3B constructs a single linear discriminant analysis (LDA) feature for the highest bin (furthest to the right) using a linear combination of the features and weighting factors within that bin. The linear combination of features and weighting factors, w, for a classifier is defined by:

$$\text{Classifier} = w_1 * \text{feature1} + w_2 * \text{feature2} + w_3 * \text{feature3} + \ldots w_n * \text{feature}N. \quad (2)$$

A block 336 applies the LDA feature to the truth sets and computes $R_d$ for the LDA feature. Finally, a block 338 constructs an expanded LDA feature using the first LDA feature with additional weighted features from the neighboring bins of the histogram. An example of this procedural step is illustrated for a histogram 600 in FIG. 6B, which shows a first LDA feature from a bin 602 being expanded to include weighted features from adjacent bins, as indicated by a dash line rectangle 604. The end result is a single feature for use as a classifier for a specific type of white blood cell with high discrimination power. The mean value of this feature is 0. Cells exhibiting characteristics like the positive truth set according to this classifier score positive, and cells which don't, score negative and are determined not to be of that type of white blood cell.

In addition to identifying a specific type of white blood cell, the same approach described above can be employed more broadly to create a classifier used to separate granulocytes from non-granulocytes, which was done when training the classifiers using donor samples, as described above. Granulocytes are a category of white blood cells characterized by granules in their cytoplasm, which includes eosinophils, neutrophils, and basophils Non-granulocytes include lymphocytes and monocytes. FIG. 7 illustrates an example 700 of a granulocyte classifier that comprises 370 features listed in part on the left side of the Figure. A graph 702 illustrates a normalized frequency for granulocytes vs. non-granulocytes based on this classifier. It will be evident that the granulocytes score positive (primarily between zero and 2) on the graph, while the non-granulocytes score negative (primarily between zero and −1).

Figure 8:
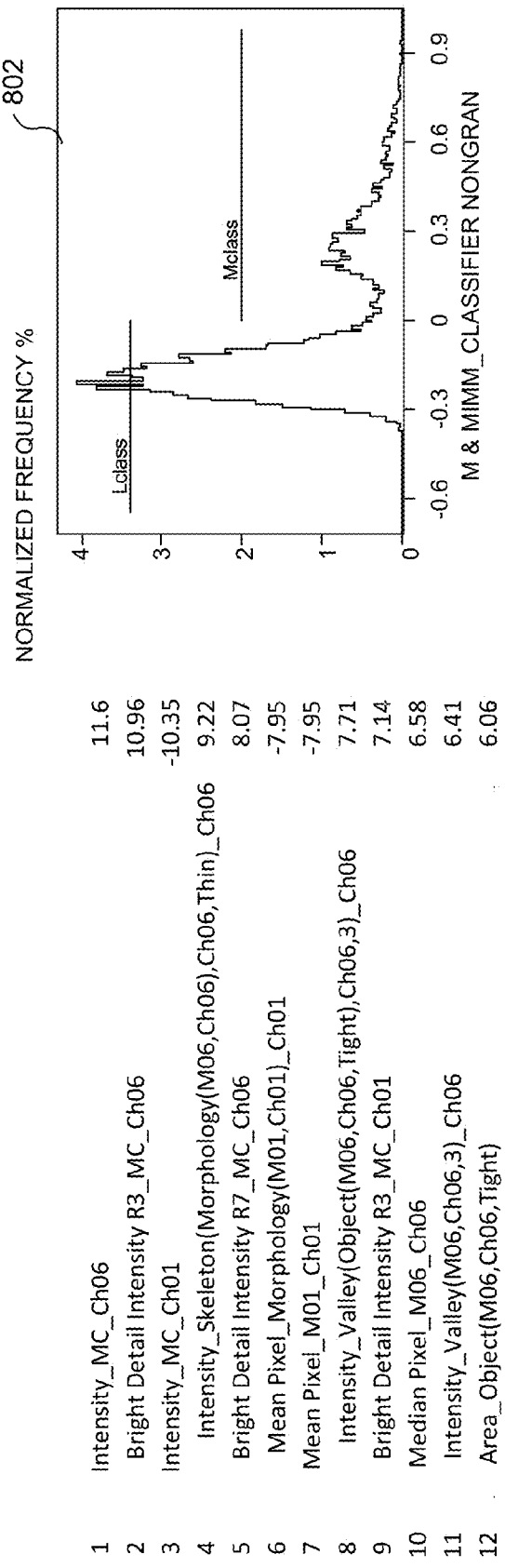
FIG. 8 is a listing of 12 features for an exemplary monocyte classifier applied to the non-granulocyte population and a graph showing how the classifier is used to distinguish between monocytes and lymphocytes in the non-granulocyte population.

FIG. 8 illustrates an example 800 of a monocyte classifier that comprises only 12 features, which are listed on the left side of the Figure. This classifier is employed only on the cells that are determined to be non-granulocytes based on the granulocyte classifier discussed above. A graph 802 illustrates a normalized frequency histogram for the monocyte classifier trained using as truths monocytes that were selected using anti-CD45 and SSC (M) that were also positive for the monocyte marker anit-CD14 (MIMM). Thus, the feature name "M & MIMM" on the horizontal axis of this graph refers to the population that was used to train the NONGRAN classifier. The portion of the curve to the right of zero (positive) indicates cells in the non-granulocyte population that are monocytes, in contrast to the negative portion of the curve that indicates cells in the non-granulocyte population that are lymphocytes.

Figure 6B:
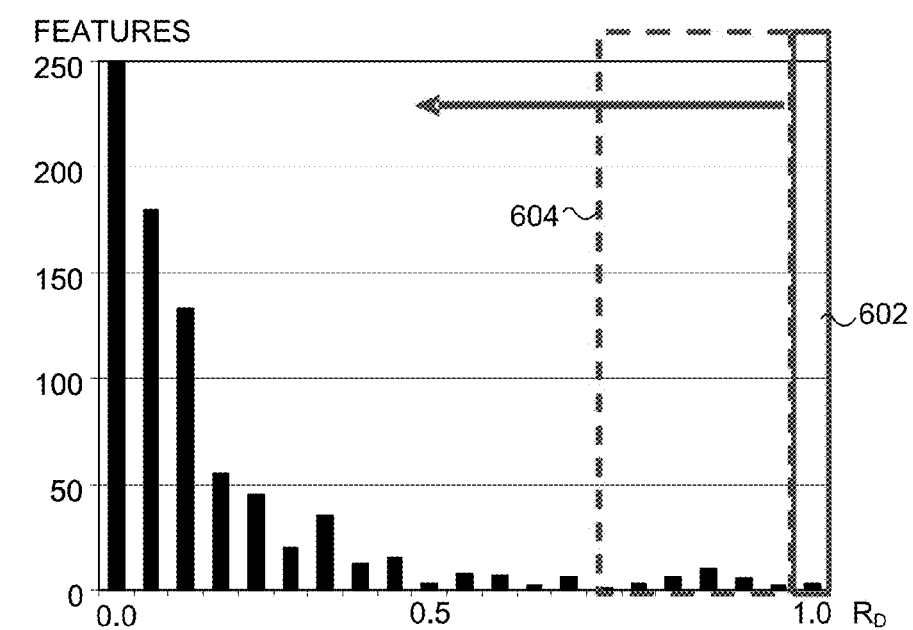
FIG. 6B is an exemplary illustration showing the construction of an expanded linear discriminant analysis feature based on the highest $R_d$ values from FIG. 6A.

FIGS. 6A and 6B illustrate how the classifiers for each type or category of white blood cell can initially be determined. After the classifiers have once been determined, they can be employed by the imaging system to automate the identification of each of the five types of white blood cells when analyzing samples of blood. An exemplary procedure for implementing such an analysis is illustrated in a flowchart 350, which is shown in FIG. 3C. The procedure begins in a start block 352 by providing a sample of whole blood for analysis. It should be noted that the analysis can be done in near real time while the sample is being processed and imaged by the imaging system, or the analysis can be completed after all of the imaging has been completed, based on stored image data that are then available for the analysis. For the sake of simplicity, this exemplary procedure assumes that the sample is being analyzed in real time. Accordingly, a block 354 loads the imaging instrument with the previously determined classifier feature sets for each type of white blood cell. Preparatory processing of the blood sample is carried out in a block 358. The preparatory processing can include formalin fixation, and permeabilization with Triton X-100 (0.1%). A block 360 provides for adding a dye such as DAPI (or other type of nuclear dye) to stain the nuclei of the white blood cells in the sample. Note that this two-step analysis methodology of initially separating the granulocytes from the non-granulocytes and then determining the individual sub-populations of each group is just an example of how classifiers generated using weighted linear combinations of image features can be used to identify specific populations. If the goal is primarily to identify populations of cells that do not fall into any of the five sub-populations of WBCs, a different approach might be to train a classifier by grouping together all five sub-populations as the positive population and everything else as the negative population. This alternative approach would then identify everything that does not fall into these five sub-populations in one step. Ultimately, the specific methodology that is selected depends on the problem that is being solved and the characteristics of the imagery. Certain populations have more distinct images compared to others and can easily be identified in one step, while others may require additional steps and additional classifiers to be created for the same sub-population in order to identify them effectively. In the present exemplary approach, basophils were difficult to identify using the two-step methodology and required multiple additional classifiers to be created in order to be able to classify them with a sufficiently high sensitivity and specificity and to obtain more consistent results. The key takeaway here is that the efficacy of the classification depends both on the actual classifier features and the analysis method that uses the classifier features.

As indicated in a block 362, a process is applied to minimize or substantially eliminate the red blood cells in the sample before the sample is imaged by the imaging system. While this process can be applied to the sample separately before the sample is ready for input to the imaging system, such as by running the sample through a centrifuge to separate the red blood cells from the white cells and reduce the excess liquid, it is more efficient to separate the red blood cells from the stream input to the imaging system in real time, before the white blood cells pass into the imaging region of the imaging system. In addition, the imaging system currently runs more optimally with a concentration of white cells that is about ten times greater than that achieved simply by removing the red blood cells from the sample, and it would be preferable to both remove the red blood cells and provide for concentration of the white blood cells inline in the flow stream of the sample supplied to the imaging system. Several techniques can be employed for this purpose. For example, excess fluid and red blood cells can be pulled from the flow stream before it enters the imaging region of the system using side sieving filtration. Since red blood cells are smaller, they will pass through a properly sized side sieve filter, along with some of the fluid, leaving a concentration of white blood cells in the central stream. Acoustic techniques can also be used to preferentially move white blood cells to the center (or to one side) of the flow stream, and a capillary tube can then be used to conduct the concentrated white blood cells in the center or side of stream into the imaging region of the system, while the red blood cells and a portion of the fluid stream are diverted away from the imaging region.

When performing the initial training of the classifiers for the various types of white blood cells, the red blood cells were lysed and then mostly removed from the sample before passing it through the imaging system. However, it is preferable not to have to lyse the red blood cells in patient samples that are subsequently processed through the imaging system. Instead, whole blood can be supplied as a sample and treated in real time—as discussed above, to separate most of the red blood cells from the white blood cells in the fluid stream actually passing through the imaging region of the imaging system. The real time processing of whole blood in this manner is much more efficient.

In a block 364 of FIG. 3C, the sample, which now comprises a concentration of mostly white blood cells is run through the imaging region of the flow cytometer imaging system, and in a block 366, the imaging system simultaneously produces bright field, side scatter, and nuclear fluorescence images of each of the cells passing through the imaging region of the flow cytometer. These images are each formed on the TDI detector as discussed above. In a block 368, the images are processed using software instructions that employ the classifiers previously determined, to identify cells from the sample being imaged as one of the five types of white blood cells, i.e., to identify a first subset of images for normal cells, or if not so identified, to include the images for any cells not identified as any type of white blood cell in a second subset designated as potentially cancerous or otherwise abnormal cells. In the present approach, the automated software processing does not attempt to classify cells in the second subset as cancerous cells, but instead simply determines that the images in the subset are not of any of the five types of white blood cells and thus, are likely not normal cells. While the processing can be carried out in real time, it is also contemplated that the image data can be stored and subsequently processed at a later time, after imaging of the cells in the sample has been completed. It should also be noted that images of any red blood cells that remain in the imaged portion of the whole blood sample will not be added to the subset of abnormal cells, since they would normally not include any nucleus and are therefore readily distinguished from potential cancerous cells, and even if immature and still retaining a nucleus, would be distinguished because of their smaller size and different shape and texture, as being part of the subset of normal cells in the sample.

Accordingly, in a block 370, the process collects a subset of image data for objects that are not included in the first subset of normal cell images, as determined by the automated processing. Finally, block 372 provides for manually reviewing the second subset of images that may be of abnormal cells, to identify any images that are likely of cancer cells in the sample. The review is carried out by skilled persons who have experience in recognizing cancerous cells by viewing the images that are provided for each such cell in the second subset. Since the second subset of potentially abnormal or cancerous cells is relatively small compared to the number of cells imaged in each sample, the effort and time required to complete the manual review is relatively small. Any determination that cells are cancerous resulting from the manual review might then be confirmed by an independent reviewer or by performing other types of tests. It is further contemplated that other cell-specific stains or dyes can be applied to a sample to enable more readily identifying or excluding any of the cells in the second subset of images as being cancerous or otherwise abnormal. The images of cancerous or abnormal cells in the second subset can then more efficiently be evaluated to make the determination or exclusion of such cellular components in the sample.

Figure 9:
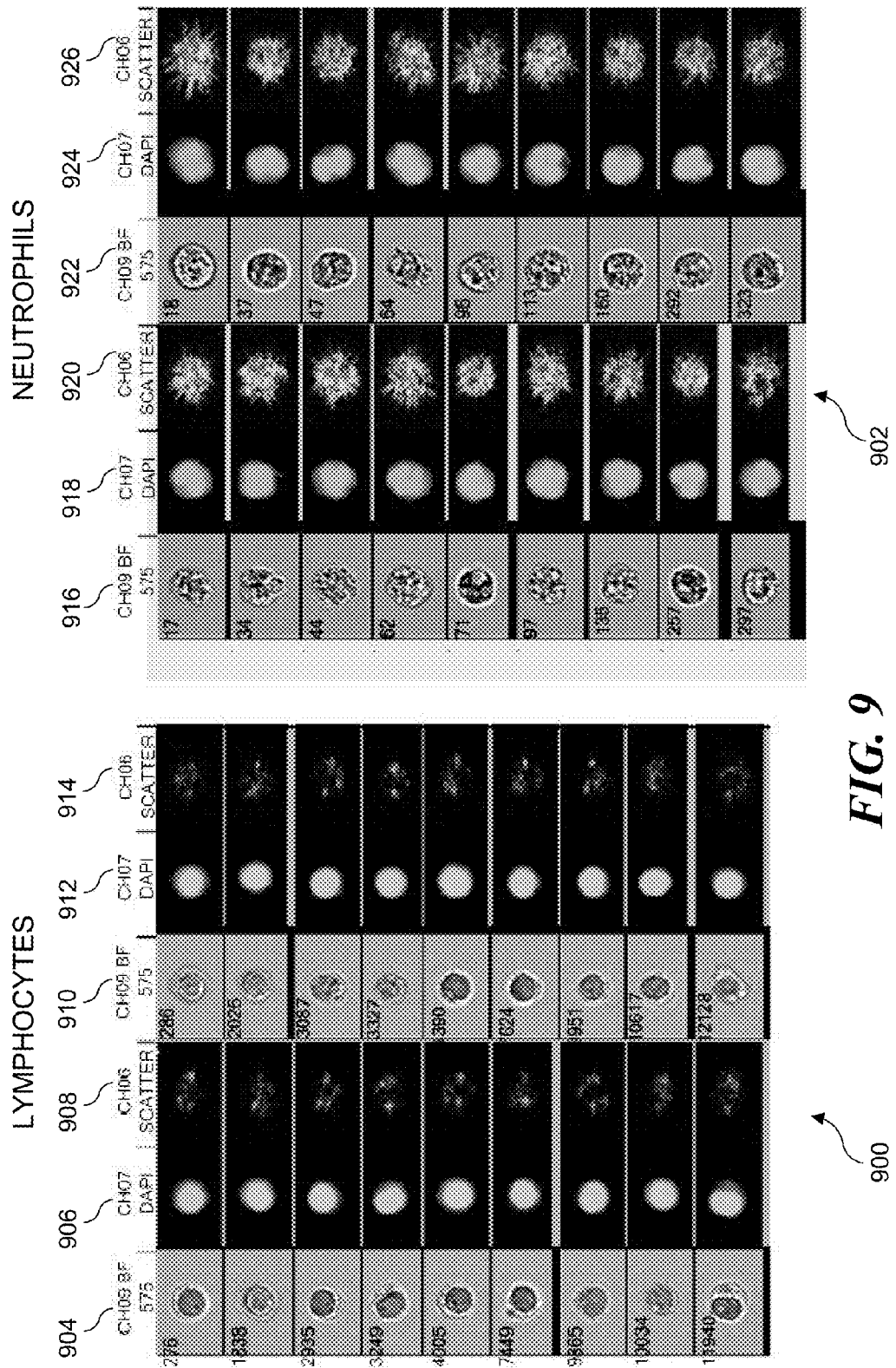
FIG. 9 is an exemplary visual review of morphological classifications for lymphocytes and neutrophils, for images in the bright field, 4',6-diamidino-2-phenylindole (DAPI) nuclear fluorescence, and side scatter channels.
Figure 10:
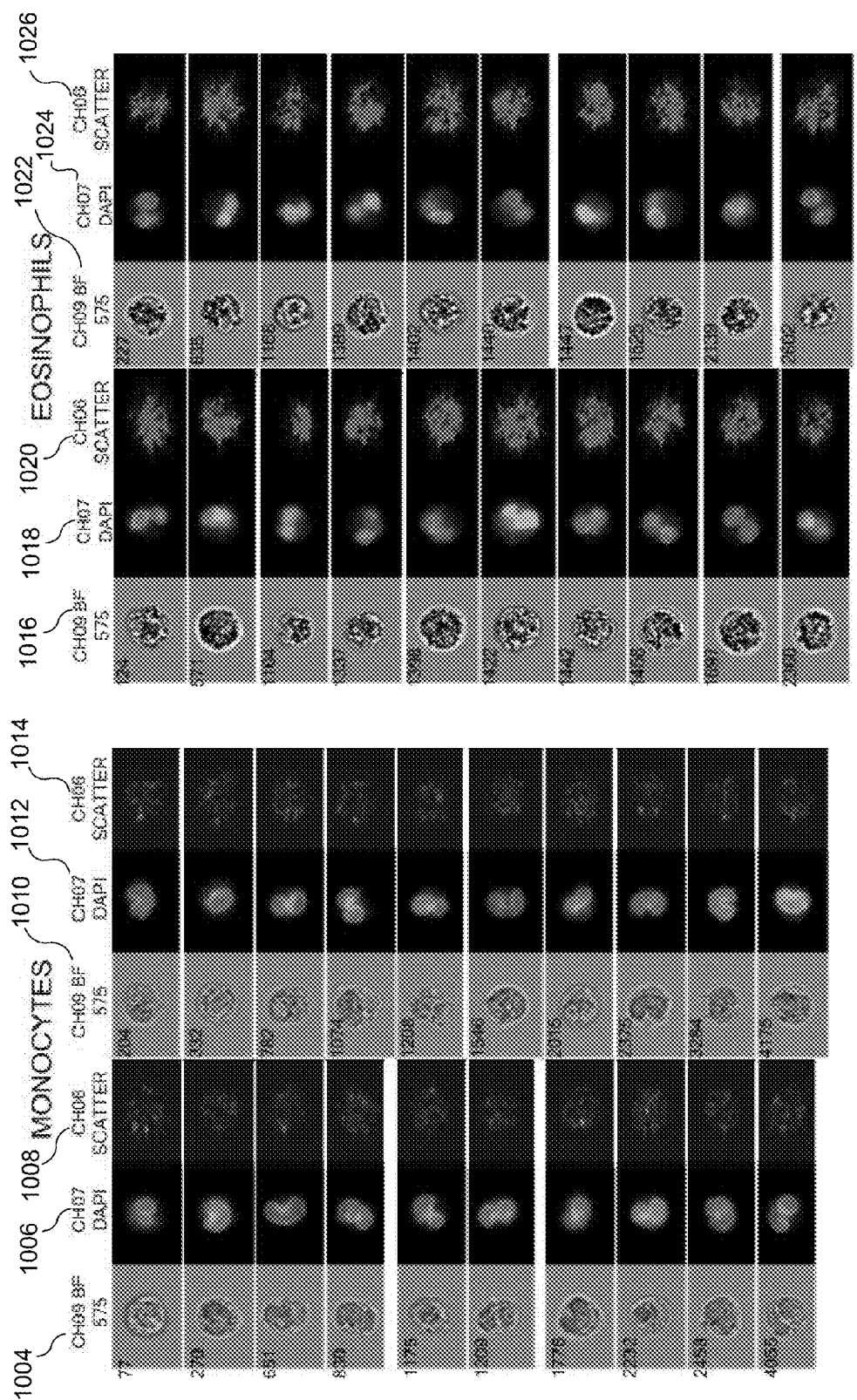
FIG. 10 is an exemplary visual review of morphological classifications for monocytes and eosinophils, for images in the bright field, DAPI, and side scatter channels.
Figure 11:
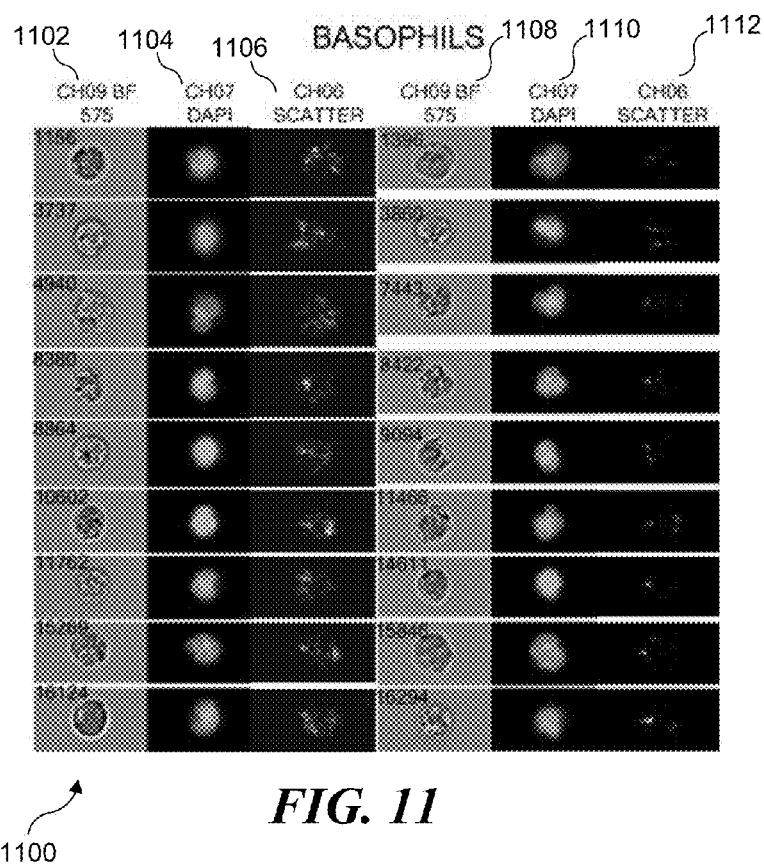
FIG. 11 is an exemplary visual review of morphological classifications for basophils, for images in the bright field, DAPI, and side scatter channels.

FIGS. 9-11 provide examples of images (gray-scale rather than the original color) showing examples for the five types of white blood cells for samples processed and identified as described using the LDA-based classifiers, and corresponding to the imaging of samples stained only with a nuclear fluorescence dye (DAPI). A set of lymphocytes images 900 in FIG. 9 includes bright field images in columns 904 and 910, nuclear fluorescence images for a nuclear stain (DAPI) in columns 906 and 912, and a set of side scatter images in columns 908 and 914, for different channels of the imaging system and for different lymphocyte cells. A set of neutrophil images 902 in FIG. 9 includes bright field images in columns 916 and 922, nuclear fluorescence images (DAPI) in columns 918 and 924, and side scatter images in columns 920 and 926.

In FIG. 10, a set of monocyte images 1000 includes bright field images in columns 1004 and 1008, nuclear fluorescence images (DAPI) in columns 1006 and 1012, and side scatter images in columns 1008 and 1014, while a set of eosinophil images 1002 includes bright field images in columns 1015 and 1022, nuclear fluorescence images in columns 1018 and 1024, and side scatter images in columns 1020 and 1026.

FIG. 11 illustrates a set of basophil images 1100 that includes bright field images in columns 1102 and 1108, nuclear fluorescence images in columns 1104 and 1110, and side scatter images in columns 1106 and 1112. While the visual differences in the appearance of the different types of white blood cells shown in FIG. 9-11 is evident, the weighted combination of features used to produce the LDA-based classifiers for each type of white blood cells provides a relatively robust approach for identifying cells of each type.

When initially developing the LDA-based classifiers as described above, it became apparent that a sufficient number of white blood cells had to be processed to improve the sensitivity for the identification of basophils Since there are very few basophils in a given sample of blood compared to the other types of white blood cells, use of only a few donor samples makes it difficult to develop an accurate classifier for basophils. This point is evident in FIG. 12, which shows a graph 1200 for whole blood—focused single cells, and a graph 1202 for lysed blood—focused single cells in regard to the intensities in the side scatter channel and in the anti-CD45 monoclonal antibody channel. In each of these graphs, an ellipse 1204 indicates the neutrophils, an ellipse 1206 indicates the lymphocytes, an ellipse 1208 indicates the basophils, an ellipse 1210 indicates the monocytes, and an ellipse 1212 indicates the eosinophils In comparing the graphs, it is apparent that basophils in the whole blood samples in graph 1200 have a higher side scatter intensity than basophils in the lysed blood samples in graph 1202. Also, graph 1200 shows that very few usable basophils were obtained in the whole blood sample, resulting in difficulty in getting robust classification results. However, by increasing the number of donor samples that were processed, a much more robust LDA-based classifier for the basophils was developed, that can now be employed for processing other samples from patients.

Sensitivity and Specificity Analysis

As discussed above, accurate identification of cells as being one of the five types of white blood cells (or something else) can be evaluated in terms of the sensitivity and specificity of the identification. FIG. 13 provides a definition of each of these terms and of the terms employed in determining each. Specifically, sensitivity is defined as the number of true positives divided by the sum of the number of true positives and the number of false negatives. Specificity is defined as the number of true negatives divided by the sum of the number of true negatives and the number of false positives. In all cases, the terms are based on subsets as defined by a gold standard, which in the exemplary procedure discussed above is based on immunofluorescence staining criteria.

Graph Illustrating Comparison of Three Criteria for Identification of WBCs

FIG. 14 graphically illustrates identification of the five types of white blood cells for eight donors. Two samples from each donor were taken. One sample was labeled with markers for the different subpopulations (anti-CD45, anti-CD14, anti-CD 123 and anti-CD193) and the nuclear stain, while the other was labeled with just the nuclear stain. The relative percentages of each subpopulation, based on the use of immunofluorescence (*IMM), a classifier that was trained on BF, SSC, and nuclear stained images (*CLASS) on the sample that had the multiple labeling, and the same classifier applied to the sample that was labeled only with the nuclear stain (*DAPI) are shown. The results illustrate how closely aligned the identification of neutrophils, lymphocytes, monocytes, and eosinophils is for all three criteria of identification. Each of these types of white blood cells are grouped using small ellipses in the Figure. Only the identification of basophils shows that there are rather significant differences between truth, i.e., the immunofluorescence criteria, and two other identification criteria, i.e., using the classifier on the sample with the multiple labels and the same classifier on the sample with only the DAPI nuclear stain. However, the classifier features more recently obtained have been improved using more donor samples for their determination compared to the results shown in FIG. 14, so that the differences between the three criteria are now also much less for basophils Exemplary Computing Device for Use in Automated Identification of White Blood Cells FIG. 15 and the following related discussion are intended to provide a brief, general description of a suitable computing environment for automating the identification of the five different types of white blood cells based on the images produced by the imaging system, where the image processing and cell type identification that is required is implemented using a computing device generally like that shown in FIG. 15. Those skilled in the art will appreciate that the required image processing and identification of the types of white blood cells may be implemented by many different types of computing devices, including a laptop and other types of portable computers, multiprocessor systems, networked computers, a server, a mainframe computer, hand-held computers, personal data assistants (PDAs), and on other types of computing devices that include a processor and a memory for storing machine instructions, which when implemented by the processor, result in the execution of a plurality of functions.

An exemplary computing system 1500 suitable for implementing the image processing required to identify white blood cells in the present approach includes a processing unit 1504 that is functionally coupled to an input device 1502, and an output device 1512, e.g., a display, or printer, or storage device for output data. Image data from the TDI detector if the images are being processed in real time, or from a storage (such as a hard drive) if previously produced by the imaging system when imaging cells are input to processing unit 1504 for processing. Processing unit 1504 include a central processing unit (CPU 1508) or other hardware logic device that executes machine instructions comprising an image processing/image analysis program for implementing the functions of the present invention (i.e., analyzing a plurality of images simultaneously collected for members of a population of objects to enable characteristics or features exhibited by members of the population to be determined and used to identify the types of objects in each image). In at least one embodiment, the machine instructions implement functions generally consistent with those described above, with reference to the automated identification of the types of white blood cells, as described in connection with the flowcharts of FIGS. 3A, 3B, and 3C. Those of ordinary skill in the art will recognize that processors or central processing units (CPUs) suitable for this purpose are available from Intel Corporation, AMD Corporation, Motorola Corporation, and from other sources.

Also included in processing unit 1504 are a random access memory 1506 (RAM) and non-volatile memory 1510, which typically includes read only memory (ROM) and some form of memory storage, such as a hard drive, optical drive, etc. These memory devices are bi-directionally coupled to CPU 1508. Such storage devices are well known in the art. Machine instructions and data are temporarily loaded into RAM 1506 from non-volatile memory 1510. Also stored in memory are the operating system software and ancillary software. While not separately shown, it should be understood that a power supply is required to provide the electrical power needed to energize computing system 1500.

Input device 1502 can be any device or mechanism that facilitates input into the operating environment, including, but not limited to, a mouse, a keyboard, a microphone, a modem, a pointing device, or other input devices. While not specifically shown in FIG. 15, it should be understood that computing system 1500 is logically coupled to an imaging system such as that schematically illustrated in FIG. 1A, so that the image data collected are available to computing system 1500 to achieve the desired image processing. Of course, rather than logically coupling the computing system directly to the imaging system, data collected by the imaging system can simply be transferred to the computing system by means of many different data transfer devices, such as portable memory media, or via a network (wired or wireless), or can be transferred from a data store. Output device 1512 will most typically comprise a monitor or computer display designed for human visual perception of an output image.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

What is claimed is:

1. A method for detecting cancerous or other types of abnormal cells in a blood sample, comprising:

(a) staining the nuclei of cells in the blood sample using a nuclear dye or stain, producing stained cells;
(b) removing red blood cells from the blood sample, leaving a residual sample comprising primarily white blood cells and a fluid;
(c) imaging the stained cells to simultaneously produce a plurality of different types of images of each stained cell;
(d) automatically evaluating the plurality of different types of images to detect features of the images, and based on classifiers previously defined as a function of features selected for distinguishing each of a plurality of different types of white blood cells, automatically identifying a first subset of the stained cells as specific types of white blood cells in the blood sample, where a second subset of cells includes cells that were not identified as being any type of white blood cell; and
(e) manually reviewing images of the second subset of cells to determine whether any of the cells in the second subset are cancerous or other type of abnormal cell.

2. The method of claim 1, further comprising using one or more other selected cell-specific stains to facilitate identifying or excluding images if the second subset as cancerous or other type of abnormal cell.

3. The method of claim 1, wherein staining the nuclei of cells in the residual sample comprises applying fixation and permeabilization of the cells before staining the nuclei with the nuclear dye or stain.

4. The method of claim 1, wherein removing the red blood cells comprises applying either a filtering process or using an acoustic technique to separate the red blood cells and excess fluid from the blood sample to produce the residual sample.

5. The method of claim 1, wherein the nuclear dye or stain comprises one of:
(a) 4',6-diamidino-2-phenylindole (DAPI);
(b) a cell-permeant cyanine nucleic acid stain;
(c) an A-T intercalating anthraquinone stain;
(d) 7-Aminoactinomycin D (7-AAD); or
(e) propidium iodide.

6. The method of claim 1, wherein imaging the stained cells to simultaneously produce a plurality of different types of images comprises processing the stained cells with a flow cytometer that forms images of cells passing through an imaging region of the flow cytometer, using light in a plurality of different channels, light in each channel being used to produce a different one of the plurality of different types of images on separate portions of a light detector.

7. The method of claim 1, wherein the plurality of different types of images that are produced include a bright field image, a side scatter image, and a nuclear fluorescence image.

8. The method of claim 1, wherein automatically evaluating the plurality of different types of images to detect features of the images comprises automatically detecting morphometric parameters and photometric parameters evident in the plurality of different types of images, and wherein identifying the first subset of the stained cells as specific types of white blood cells in the blood sample comprises applying the classifiers previously determined to the morphometric and photometric parameters detected in the images of the cells, where each classifier is applied to detect a different type of white blood cell.

9. The method of claim 8, further comprising using linear discriminant analysis to determine the classifiers for each different type of white blood cell, to form a weighted linear combination of selected features for each classifier.

10. The method of claim 9, wherein the features were previously selected for determining each classifier for each different type of white blood cell by evaluating populations of donor blood cells that were stained with both the nuclear dye or stain, and with monoclonal antibodies appropriate for identifying each type of white blood cell, using features related to the monoclonal antibodies to identify each different type of white blood cells in the populations of donor cells, and then selecting specific features related to the nuclear dye or stain for each type of white blood cell thus identified that provided a greatest discrimination relative to other types of white blood cells, for use in the linear weighted combination of features used for a classifier for that type of white blood cell.

11. Apparatus for use in facilitating detection of cancerous or other types of abnormal cells in a blood sample, comprising:
(a) an image acquisition subsystem configured to simultaneously acquire a plurality of different types of images of individual cells in the blood sample, where the individual cells have been stained with a nuclear dye or stain, the plurality of different types of images exhibiting morphometric and photometric parameters characteristic of the type of cell being imaged; and
(b) a programmed image processing system for automatically identifying white blood cells in the blood sample, based on selected features derived from the morphometric and photometric parameters detected in the different types of images, using predefined classifiers that employ the selected features for each different type of white blood cell, the programmed image processing system also designating images for any remaining cells in the blood sample that were not automatically identified as any type of white cell, for subsequent manual review that can determine if any of the remaining cells are cancerous or abnormal.

12. The apparatus of claim 11, further comprising a red blood cell separator disposed upstream of an imaging region in the image acquisition subsystem, the red blood cell separator removing red blood cells from the blood sample that passes into the imaging region.

13. The apparatus of claim 12, wherein the red blood cell separator comprises either a filter with a filter screen sized to pass red blood cells but not white blood cells, or an acoustic separator that applies an acoustic force to shift the red blood cells and the white blood cells in a flow of fluid entering the imaging region apart, so that mostly white blood cells enter the imaging region and the red blood cells do not.

14. The apparatus of claim 12, wherein the red blood cell separator also reduces an amount of fluid included in the blood sample entering the imaging region, to increase a concentration of the white blood cells being imaged by the image acquisition subsystem.

15. The apparatus of claim 11, wherein the plurality of different types of images include:
(a) bright field images;
(b) side scatter images; and
(c) nuclear fluorescence images.

16. The apparatus of claim 11, wherein the image acquisition subsystem includes a beam splitter and a plurality of optical filters for creating different light paths to create the plurality of different types of images.

17. The apparatus of claim 11, wherein the predefined classifiers employed by the programmed image processing system for identifying each type of white blood cell are based on a linear discriminant analysis and are a linear weighted combination of the selected features for each type of white blood cell, the selected features having been previously identified as providing greater discrimination between one type of white blood cells and other types of white blood cells.

18. A method for determining classifiers for identifying each type of white blood cell in a sample of blood, comprising:
(a) providing a donor blood sample;
(b) labeling white blood cells in the donor sample with a nuclear dye or stain, and with monoclonal antibodies selected for identification of each type of white blood cell, producing a stained sample;
(c) substantially reducing a number of red blood cells in the stained sample, producing a residual sample;
(d) processing cells in the residual sample using an imaging system that simultaneously produces a set of different types of images for each white blood cell that is imaged by the imaging system, the set including a bright field image, a side scatter image, an immunofluorescence image, and a nuclear fluorescence image;
(e) using the immunofluorescence images to determine truth in regard to identification of the white blood cells included in the residual sample;
(f) analyzing the bright field, side scatter, and nuclear fluorescence images to detect photometric and morphometric parameters comprising features for each type of white blood cells that was identified; and
(f) based on selected features detected, defining a classifier for each type of white blood cell, for use in automated identification of white blood cells labeled with the nuclear dye or stain that are included in subsequent samples processed with the imaging system.

19. The method of claim 18, wherein defining the classifier for each type of white blood cell comprises using a linear discriminant analysis to produce a linear weighted combination of selected features identified in the bright field, side scatter, and nuclear fluorescence images.

20. The method of claim 19, wherein the features are selected for each type of white blood cell based on their ability to discriminate a type of white blood cell from other types of white blood cells.

21. The method of claim 18, wherein the monoclonal antibodies used for labeling the white blood cells in the residual sample comprise:
(a) an anti-CD45 monoclonal antibody;
(b) an anti-CD14 monoclonal antibody;
(c) an anti-CD123 monoclonal antibody; and
(d) an anti-CD193 monoclonal antibody.

22. The method of claim 18, wherein the nuclear dye or stain comprises one of:
(a) 4',6-diamidino-2-phenylindole (DAPI);
(b) a cell-permeant cyanine nucleic acid stain;
(c) an A-T intercalating anthraquinone stain;
(d) 7-Aminoactinomycin D (7-AAD); or
(e) propidium iodide.

23. The method of claim 18, wherein reducing the number of red blood cells in the donor blood sample to produce the residual sample comprises at least one selected from the group consisting of:
(a) subjecting the stained sample to an acoustic force that shifts the red blood cells out of a flow stream entering an imaging region of the imaging system;
(b) filtering the stained sample with a filter screen sized to allow the red blood cells that are smaller than the white blood cells to pass through the filter screen, while blocking the white blood cells, so that the white blood cells are conveyed by the flow stream into the imaging region of the imaging system, but the red blood cells are not; and
(c) lysing the red blood cells in the donor blood sample and separating lysed red blood cells from the white blood cells using centrifugal force.

24. The method of claim 18, further comprising applying fixation and permeabilization of the white blood cells before labeling the white blood cells with the nuclear dye or stain and with the monoclonal antibodies.

25. The method of claim 18, further comprising collecting additional donor blood samples and repeating the method of claim 18 for the additional donor blood samples to improve a sensitivity and specificity of the classifier used for identifying each type of white blood cell in blood samples subsequently processed by the imaging system.

* * * * *